(12) United States Patent
Ahlqvist et al.

(10) Patent No.: US 7,763,597 B2
(45) Date of Patent: *Jul. 27, 2010

(54) SALTS

(75) Inventors: Matti Ahlqvist, Molndal (SE); Martin Bohlin, Molndal (SE); Tord Inghardt, Molndal (SE); Anita Lundblad, Molndal (SE); Carl-Gustaf Sigfridsson, Molndal (SE)

(73) Assignee: AstraZeneca AB, Sodertalje (SE)

( * ) Notice: Subject to any disclaimer, the term of this patent is extended or adjusted under 35 U.S.C. 154(b) by 24 days.

This patent is subject to a terminal disclaimer.

(21) Appl. No.: 11/839,842

(22) Filed: Aug. 16, 2007

(65) Prior Publication Data

US 2008/0269176 A1    Oct. 30, 2008

Related U.S. Application Data

(63) Continuation of application No. 10/516,422, filed as application No. PCT/SE03/00859 on May 27, 2003, now Pat. No. 7,273,858.

(30) Foreign Application Priority Data

May 31, 2002   (SE) .................................... 0201661

(51) Int. Cl.
   A61K 31/397   (2006.01)
   A61K 31/60    (2006.01)
   A61P 7/02     (2006.01)
(52) U.S. Cl. ................................. 514/161; 514/210.17
(58) Field of Classification Search .................. None
   See application file for complete search history.

(56) References Cited

U.S. PATENT DOCUMENTS

| 4,346,078 | A | 8/1982 | Bajusz et al. |
|---|---|---|---|
| 4,703,036 | A | 10/1987 | Bajusz et al. |
| 4,792,452 | A | 12/1988 | Howard et al. |
| 5,053,416 | A | 10/1991 | Toja et al. |
| 5,260,307 | A | 11/1993 | Ackermann et al. |
| 5,393,760 | A | 2/1995 | Ackermann et al. |
| 5,405,854 | A | 4/1995 | Ackermann et al. |
| 5,498,724 | A | 3/1996 | Nystrom et al. |
| 5,532,232 | A | 7/1996 | Ackermann et al. |
| 5,559,232 | A | 9/1996 | Ackermann et al. |
| 5,578,594 | A | 11/1996 | Ackermann et al. |
| 5,583,133 | A | 12/1996 | Ackermann et al. |
| 5,595,999 | A | 1/1997 | Ackermann et al. |
| 5,602,253 | A | 2/1997 | Antonsson et al. |
| 5,659,071 | A | 8/1997 | Nystrom et al. |
| 5,677,448 | A | 10/1997 | Ackermann et al. |
| 5,705,487 | A | 1/1998 | Schacht et al. |
| 5,707,966 | A | 1/1998 | Schacht et al. |
| 5,710,130 | A | 1/1998 | Schacht et al. |
| 5,723,444 | A | 3/1998 | Antonsson et al. |
| 5,744,487 | A | 4/1998 | Ohshima et al. |
| 5,763,436 | A | 6/1998 | Ackermann et al. |
| 5,763,604 | A | 6/1998 | Ackermann et al. |
| 5,780,631 | A | 7/1998 | Antonsson et al. |
| 5,783,563 | A | 7/1998 | Antonsson et al. |
| 5,856,307 | A | 1/1999 | Antonsson et al. |
| 5,939,392 | A | 8/1999 | Antonsson et al. |
| 5,965,692 | A | 10/1999 | Gustafsson et al. |
| 6,030,972 | A | 2/2000 | Bohm et al. |
| 6,034,104 | A | 3/2000 | Klimkowski et al. |
| 6,051,568 | A | 4/2000 | Gustafsson et al. |
| 6,083,532 | A | 7/2000 | Zhang et al. |
| 6,221,898 | B1 | 4/2001 | Antonsson |
| 6,225,287 | B1 | 5/2001 | Edvardsson et al. |
| 6,255,301 | B1 | 7/2001 | Gustafsson et al. |
| 6,262,028 | B1 | 7/2001 | Antonsson et al. |
| 6,265,397 | B1 | 7/2001 | Karlsson et al. |
| 6,287,599 | B1 | 9/2001 | Burnside et al. |
| 6,337,343 | B1 | 1/2002 | Gustafsson et al. |
| 6,337,394 | B2 | 1/2002 | Karlsson et al. |
| 6,433,186 | B1 | 8/2002 | Inghardt et al. |
| 6,440,937 | B1 | 8/2002 | Baucke et al. |
| 6,440,939 | B2 | 8/2002 | Edvardsson et al. |
| 6,444,817 | B1 | 9/2002 | Bohm et al. |

(Continued)

FOREIGN PATENT DOCUMENTS

EP    0185390    10/1991

(Continued)

OTHER PUBLICATIONS

Baveja et al. "Zero-order release hydrophilic matrix tablets of beta-adrenergic blockers" International Journal of Pharmaceutics 39:39-45 (1987).

(Continued)

*Primary Examiner*—Kamal A Saeed
(74) *Attorney, Agent, or Firm*—Morgan Lewis & Bockius LLP

(57) ABSTRACT

There is provided pharmaceutically-acceptable acid addition salts of compounds of formula (I),

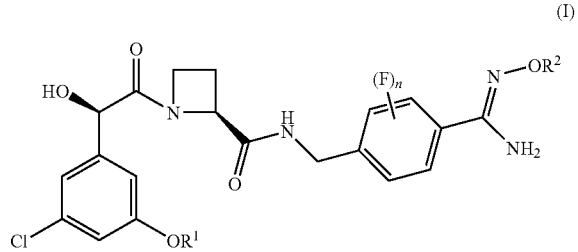

(I)

wherein $R^1$ represents $C_{1-2}$ alkyl substituted by one or more fluoro substituents; $R^2$ represents $C_{1-2}$ alkyl; and n represents 0, 1 or 2, which salts are useful as prodrugs of competitive inhibitors of trypsin-like proteases, such as thrombin, and thus, in particular, in the treatment of conditions where inhibition of thrombin is required.

22 Claims, 5 Drawing Sheets

U.S. PATENT DOCUMENTS

| | | | |
|---|---|---|---|
| 6,455,671 B1 | 9/2002 | Bohm et al. |
| 6,479,078 B1 | 11/2002 | Hedstrom et al. |
| 6,521,253 B1 | 2/2003 | Forsman et al. |
| 6,576,245 B1 | 6/2003 | Lundgren et al. |
| 6,576,657 B2 | 6/2003 | Karlsson et al. |
| 6,599,894 B1 | 7/2003 | Inghardt et al. |
| 6,617,320 B2 | 9/2003 | Gustafsson et al. |
| 6,660,279 B2 | 12/2003 | Lundgren et al. |
| 6,716,834 B2 | 4/2004 | Andersson et al. |
| 6,750,243 B1 | 6/2004 | Inghardt et al. |
| 6,811,794 B2 | 11/2004 | Burnside et al. |
| 6,838,478 B2 | 1/2005 | Gustafsson et al. |
| 6,875,446 B2 | 4/2005 | Forsman et al. |
| 6,888,007 B2 | 5/2005 | Edvardsson et al. |
| 6,921,758 B2 | 7/2005 | Gustafsson et al. |
| 6,984,627 B1 | 1/2006 | Antonsson et al. |
| 6,998,136 B2 | 2/2006 | Lundgren et al. |
| 7,056,907 B2 | 6/2006 | Inghardt et al. |
| 7,129,233 B2 | 10/2006 | Inghardt et al. |
| 7,202,236 B2 | 4/2007 | Magnusson et al. |
| 7,273,858 B2 | 9/2007 | Ahlqvist et al. |
| 2003/0004308 A1 | 1/2003 | Bohm et al. |
| 2004/0019033 A1 | 1/2004 | Inghardt et al. |
| 2004/0242492 A1 | 12/2004 | Inghardt et al. |
| 2004/0242536 A1 | 12/2004 | Khoo et al. |
| 2005/0171083 A1 | 8/2005 | Magnusson et al. |
| 2006/0014734 A1 | 1/2006 | Alami et al. |
| 2006/0111553 A1 | 5/2006 | Boehm et al. |
| 2007/0202174 A1 | 8/2007 | Inghardt et al. |
| 2007/0218136 A1 | 9/2007 | Inghardt et al. |
| 2008/0050437 A1 | 2/2008 | Magnusson et al. |
| 2008/0090800 A1 | 4/2008 | Inghardt et al. |
| 2008/0287413 A1 | 11/2008 | Aslund et al. |
| 2008/0293965 A1 | 11/2008 | Bosson |
| 2008/0312457 A1 | 12/2008 | Blixt et al. |
| 2008/0319206 A1 | 12/2008 | Al-Saffar et al. |

FOREIGN PATENT DOCUMENTS

| | | |
|---|---|---|
| EP | 0526877 | 2/1993 |
| EP | 0293881 | 3/1993 |
| EP | 0530167 | 3/1993 |
| EP | 0539059 | 4/1993 |
| EP | 0195212 | 11/1993 |
| EP | 0468231 | 9/1994 |
| EP | 0641779 | 3/1995 |
| EP | 0648780 | 4/1995 |
| EP | 0362002 | 7/1995 |
| EP | 0686642 | 12/1995 |
| EP | 0364344 | 5/1998 |
| EP | 0542525 | 7/1998 |
| EP | 0559046 | 7/2001 |
| EP | 0669317 | 9/2002 |
| EP | 0773955 | 4/2003 |
| EP | 0672658 | 9/2003 |
| JP | 57149217 | 9/1982 |
| WO | WO 93/11152 | 6/1993 |
| WO | WO 93/18060 | 9/1993 |
| WO | WO 94/29269 | 12/1994 |
| WO | WO 94/29336 | 12/1994 |
| WO | WO 95/23609 | 9/1995 |
| WO | WO 95/35309 | 12/1995 |
| WO | WO 96/03374 | 2/1996 |
| WO | WO 96/25426 | 8/1996 |
| WO | WO 96/26717 | 9/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/39770 | 10/1997 |
| WO | WO 97/46577 | 12/1997 |
| WO | WO 97/49404 | 12/1997 |
| WO | WO 98/01422 | 1/1998 |
| WO | WO 98/06740 | 2/1998 |
| WO | WO 98/16252 | 4/1998 |
| WO | WO 98/57932 | 12/1998 |
| WO | WO 99/21586 | 5/1999 |
| WO | WO 99/27913 | 6/1999 |
| WO | WO 99/29305 | 6/1999 |
| WO | WO 99/29664 | 6/1999 |
| WO | WO 99/39698 | 8/1999 |
| WO | WO 00/12043 | 3/2000 |
| WO | WO 00/13671 | 3/2000 |
| WO | WO 00/13710 | 3/2000 |
| WO | WO 00/14110 | 3/2000 |
| WO | WO 00/18352 | 4/2000 |
| WO | WO 00/35869 | 6/2000 |
| WO | WO 00/42059 | 7/2000 |
| WO | WO 01/02426 | 1/2001 |
| WO | WO 01/87879 | 11/2001 |
| WO | WO 02/14270 | 2/2002 |
| WO | WO 02/19990 | 3/2002 |
| WO | WO 02/44145 | 6/2002 |
| WO | WO 03/000293 | 1/2003 |
| WO | WO 03/018551 | 3/2003 |
| WO | WO 03/090723 | 11/2003 |
| WO | WO 03/101423 | 12/2003 |
| WO | WO 03/101424 | 12/2003 |
| WO | WO 03/101957 | 12/2003 |
| WO | WO 2005/054168 | 6/2005 |
| WO | WO 2006/090153 | 8/2006 |
| WO | WO 2006/125964 | 11/2006 |
| WO | WO 2008/068475 | 6/2008 |

OTHER PUBLICATIONS

Bonferoni et al. "On the employment of lambda-carrageenan in a matrix system. II. Lambda-Carrageenan and hydroxypropylmethylcellulose mixtures" J. Controlled Release 30:175-182 (1994).

Berge et al. "Pharmaceutical Salts" J. of Pharmaceutical Sciences 66(1): 1-19 (1977).

Bonferoni et al. "On the employment of lambda-carrageenan in a matrix system. II. Lambda-Carrageenan and hydroxypropylmethylcellulose mixtures" J. Controlled Release 30:175-182 (1994).

Ham-Yong Park et al. "Effect of pH on Drug Release From Polysaccharide Tablets" Drug Delivery 5:13-18 (1998).

Picker "The use of carrageenan in mixture with microcrystalline cellulose and its functionality for making tablets" European J Pharmaceutics and Biopharmaceutics 48(1):27-36 (1999).

Talukdar et al. "In vivo evaluation of xanthan gum as a potential excipient for oral controlled-release matrix tablet formulation" International Journal of Pharmaceutics 169(1):105-113 (1998).

CAS RN 159776-70-2 Dec. 1994.

CAS RN 192939-72-3 Aug. 1997.

CAS RN 30318-53-4 Nov. 2000.

Gupta et al. "Controlled-release tablets from carrageenans: effect of formulation, storage and dissolution factors" Eur. J. Pharm. Biopharm., 51(3):241-248 (2001).

Talukdar et al. "Comparative study on xanthan gum and hydroxypropylmethyl cellulose as matrices for controlled-release drug delivery I. Compaction and in vitro drug release behaviour" International Journal of Pharmaceutics, 129(2):233-241 (1996).

Deinum et al. "Biochemical and pharmacological effects of the direct thrombin inhibitor AR-H067637" Thromb Haemost. 101(6):1051-1059 (2009).

Eriksson et al. "Comparative pharmacodynamics and pharmacokinetics of oral direct thrombin and factor Xa inhibitors in development" Clinical Pharmacokinetics 48(1):1-22 (2009).

Gyzander et al. "Enzyme kinetic characterisation of the active form of the novel oral direct thrombin inhibitor AZD0837" Journal of Thrombosis and Haemostasis, 5 Supplement 2: P-S-066 (2007).

Hockings et al. "The oral direct thrombin inhibitor AZD0837 reduces thrombus formation in a rat model" Journal of Thrombosis and Haemostasis, 5 Supplement 2: P-S-697 (2007).

Lip et al. "The oral direct thrombin inhibitor AZD0837 for the prevention of stroke and systemic embolism in patients with atrial fibrillation: A phase II randomized dose-guiding, safety and tolerability study" Journal of the American College of Cardiology 53(10, Suppl. 1):A430 (2009).

Mattsson et al. "Characterisation of the active form of the novel oral direct thrombin inhibitor AZD0837 in coagulation assays" Journal of Thrombosis and Haemostasis, 5 Supplement 2: P-T-636 (2007).

Olsson et al. "Safety and tolerability of the oral direct thrombin inhibitor AZD0837 in prevention of stroke and other thromboembolic complications associated with atrial fibrillation (AF)" Journal of Thrombosis and Haemostasis, 5 Supplement 2: O-W-053 (2007).

Patani et al. "Bioisosterism: A rational approach in drug design" Chem. Rev. 96(8):3147-3176 (1996).

Pehrsson et al. "The antithrombotic effect of AR-H067637, the active form of the novel oral direct thrombin inhibitor AZD0837, in rat models of arterial and venous thrombosis" Journal of Thrombosis and Haemostasis, 5 Supplement 2 : P-W-637 (2007).

Schutzer et al. "Effect of the oral direct thrombin inhibitor AZD0837 on glomerular filtration rate in elderly healthy subjects" Journal of Thrombosis and Haemostasis, 5 Supplement 2: P-W-668 (2007).

Wagenvoord et al. "The effect of direct thrombin inhibitors (DTIS) in clotting plasma" Journal of Thrombosis and Haemostasis, 5 Supplement 2: P-W-654 (2007).

Walfridsson et al. "Assessment of the electrophysiological effects of the oral direct thrombin inhibitor AZD0837, in subjects undergoing an invasive electrophysiological procedure" Journal of Thrombosis and Haemostasis, 5 Supplement 2 : P-W-674 (2007).

SALTS

RELATED APPLICATIONS

This is a continuation application of U.S. application Ser. No. 10/516,422, filed May 20, 2005 now U.S. Pat. No. 7,273,858, which is a U.S. National Phase Application of International Application No. PCT/SE03/00859, filed May 27, 2003), which claims the benefit of Swedish Application No. 0201661-6, filed May 31, 2002, all of which are herein incorporated by reference in their entireties.

FIELD OF THE INVENTION

This invention relates to new salts of compounds that inhibit thrombin following administration to mammalian patients, to pharmaceutical compositions containing such salts, and to processes for obtaining them.

BACKGROUND TO THE INVENTION AND PRIOR ART

In the formulation of drug compositions, it is important for the drug substance to be in a form in which it can be conveniently handled and processed. This is of importance, not only from the point of view of obtaining a commercially-viable manufacturing process, but also from the point of view of subsequent manufacture of pharmaceutical formulations comprising the active compound.

Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

The skilled person will appreciate that, typically, if a drug can be readily obtained in a stable form, such as a stable crystalline form, advantages may be provided, in terms of ease of handling, ease of preparation of suitable pharmaceutical formulations, and a more reliable solubility profile.

International Patent Application No. PCT/SE01102657 (WO 02/44145, earliest priority date 1 Dec. 2000, filed 30 Nov. 2001, published 6 Jun. 2002) discloses a number of compounds that are, or are metabolised to compounds which are, competitive inhibitors of trypsin-like proteases, such as thrombin. The following three compounds are amongst those that are specifically disclosed:

(a) Ph(3-Cl)(5-OCHF$_2$)—(R)CH(OH)C(O)—(S) Aze-Pab(OMe)

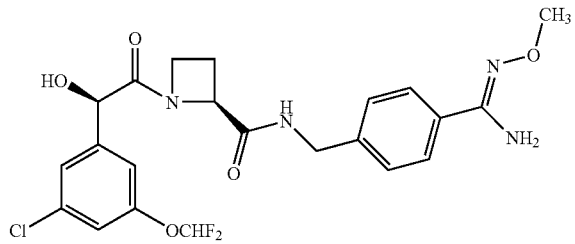

which compound is referred to hereinafter as Compound A;

(b) Ph(3-Cl)(5-OCHF$_2$)—(R)CH(OH)C(O)—(S) Aze-Pab(2,6-diF)(OMe)

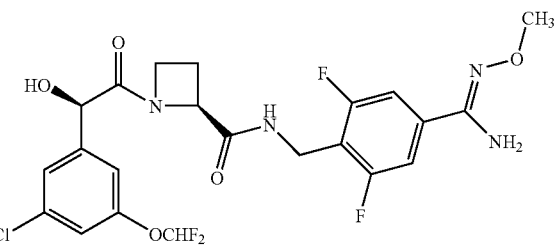

which compound is referred to hereinafter as Compound B; and (c) Ph(3-Cl)(5-OCH$_2$CH$_2$F)—(R)CH(OH)C(O)—(S) Aze-Pab(OMe)

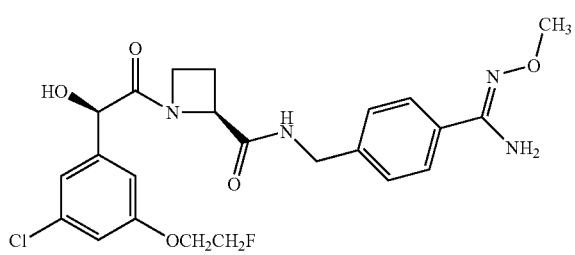

which compound is referred to hereinafter as Compound C.

Abbreviations are listed at the end of this specification.

The methoxyamidine Compounds A, B and C are metabolised following oral and/or parenteral administration to the corresponding free amidine compounds, which latter compounds have been found to be potent inhibitors of thrombin.

Processes for the synthesis of Compounds A, B and C are described in Examples 12, 40 and 22 (respectively) of International Patent Application No. PCT/SE01/02657.

Specific pharmaceutically acceptable salts of Compounds A, B and C are not disclosed in PCT/SE01/02657. Further, no information is provided in relation to how crystalline forms of Compounds A, B or C, and particularly salts thereof, may be prepared.

DISCLOSURE OF THE INVENTION

According to a first aspect of the invention, there is provided a pharmaceutically-acceptable acid addition salt of a compound of formula I,

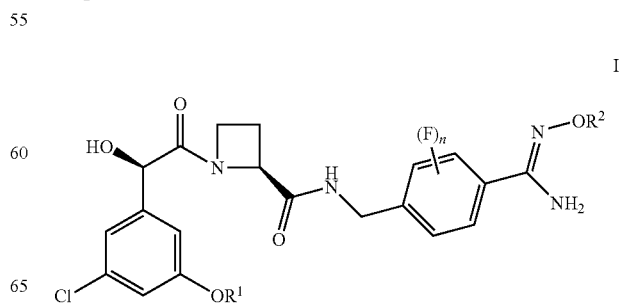

wherein

R¹ represents $C_{1-2}$ alkyl substituted by one or more fluoro substituents;

R² represents $C_{1-2}$ alkyl; and n represents 0, 1 or 2;

which salts are referred to hereinafter as "the compounds of the invention".

The compounds of the invention may be in the fort of a solvate, a hydrate, a mixed solvate/hydrate or, preferably, an ansolvate, such as an anhydrate. Solvates may be of one or more organic solvents, such as lower (erg. $C_{1-4}$) alkyl alcohols (e.g. methanol, ethanol or iso-propanol), ketones (such as acetone), esters (such as ethyl acetate) or mixtures thereof. Additionally, tautomers of the compounds of the invention are also included.

Preferred acid addition salts include inorganic acid addition salts, such as those of sulphuric acid, nitric acid, phosphoric acid and hydrohalic acids, such as hydrobromic acid and hydrochloric acid. More preferred acid addition salts include those of organic acids, such as those of dimethylphosphoric acid; saccharinic acid; cyclohexylsulfamic acid; those of carboxylic acids (such as maleic acid, fumaric acid, aspartic acid, succinic acid, malonic acid, acetic acid, benzoic acid, terephthalic acid, hippuric acid, 1-hydroxy-2-naphthoic acid, pamoic acid, hydroxybenzoic acid and the like); those of hydroxy acids (such as salicylic acid, tartaric acid, citric acid, malic acid (including L-(−)-malic acid and, D,L-malic acid), gluconic acid (including D-gluconic acid), glycolic acid, ascorbic acid, lactic acid and the like), those of amino acids (such as glutamic acid (including D-glutamic, L-glutamic, and D,L-glutamic, acids), arginine (including L-arginine), lysine (including L-lysine and L-lysine hydrochloride), glycine and the like); and, particularly, those of sulfonic acids, (such as 1,2-ethanedisulfonic acid, camphorsulfonic acids (including 1S-(+)-10-camphorsulfonic acid and (+/−)-camphorsulfonic acids), ethanesulfonic acid, a propanesulfonic acid (including n-propanesulfonic acid), a butanesulfonic acid, a pentanesulfonic acid, a toluenesulfonic acid, methanesulfonic acid, p-xylenesulfonic acid, 2-mesitylenesulfonic acid, naphthalenesulfonic acids (including 1,5-naphthalenesulfonic acid and 1-naphthalenesulfonic acid), benzenesulfonic acid, hydroxybenzenesulfonic acids, 2-hydroxyethanesulfonic acid, 3-hydroxyothanesulfonic acid and the like), Particularly preferred salts include those of $C_{1-6}$ (e.g. $C_{1-4}$) alkanesulfonic acids, such as ethanesulfonic acid and propanesulfonic acid (e.g. n-propanesulfonic acid) and optionally substituted (e.g. with one or more $C_{1-2}$ alkyl groups) arylsulfonic acids, such as benzenesulfonic acid.

Further particularly preferred salts include those of $C_{1-6}$ (e.g. $C_{1-4}$ alkanesulfonic acids, such as ethanesulfonic acid and propanesulfonic acid (e.g. n-propanesulfonic acid), optionally substituted (e.g. with one or more $C_{1-2}$ alkyl groups) arylsulfonic acids, such as benzenesulfonic acid, and optionally substituted (e.g. with one or more $C_{1-2}$ alkyl groups) aryldisulfonic acids, such as 1,5-naphthalenedisulfonic acid (and hemi-1,5-naphthalenedisulfonic acid)

Preferred compounds of formula I include those in which:

R¹ represents —OCHF₂ or —OCH₂CH₂F;

R² represents methyl;

n represents 0 or 2.

More preferred compounds of formula I include those in which n represents 0, or those in which n represents 2, so providing two fluoro atoms located at the 2- and 6-positions (i.e. the two ortho-positions relative to the point of attachment of the benzene ring to the —NH—CH₂— group).

Particularly preferred compounds of formula I include Compound B, Compound C and, especially, Compound A.

Compounds of the invention may be made by way of techniques, which may comprise addition of an appropriate amount of the relevant acid to a compound of formula I in free base form, for example as described hereinafter; conversion of one salt to another (in the case where there is difference in the pKa values of the relevant acids and the solubilities of the respective salts); and ion pair chromatography.

According to a further aspect of the invention, there is provided a process for the preparation of a compound of the invention, which comprises addition of an acid to a compound of formula I.

Suitable stoichiometric ratios of acid to free base are in the range 0.25:1.5 to 30:1, such as 0.45:1.25 to 1.25:1, including 0.50:1 to 1:1.

Compounds of formula I may be prepared by the following processes (relevant information is also incorporated herein from International Patent Application No. PCT/SE01/02657 (WO 02/44145, earliest priority date 1 Dec. 2000, filed 30 Nov. 2001, published 6 Jun. 2002)):

(i) the coupling of a compound of formula II,

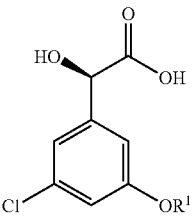

II wherein R¹ is as hereinbefore defined with a compound of formula III,

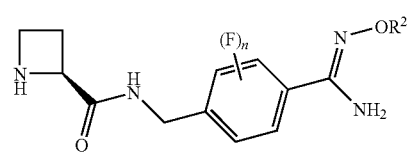

III wherein n and R² are as hereinbefore defined, for example in the presence of a coupling agent (e.g. oxalyl chloride in DAF, EDC, DCC, HBTU, HATU, PyBOP or TBTU), an appropriate base (e.g. pyridine, DMAP, TEA, 2,4,6-collidine or DIPEA) and a suitable organic solvent (e.g. dichloromethane, acetonitrile, EtOAc or DMF);

(ii) the coupling of a compound of formula By

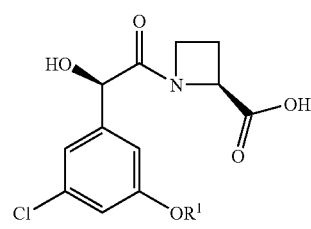

IV wherein R¹ is as hereinbefore defined with a compound of formula V,

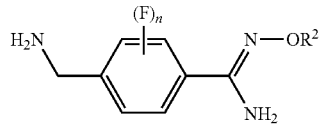

V wherein n and R² are as hereinbefore defined, for example under conditions as described in process (i) above, or (iii) reaction of a protected derivative of a compound corresponding to a compound of formula I, except that, in place of the group OR², a H atom is present (i.e. a corresponding free amidine compound), which protected derivative is, for example, a compound of formula VI,

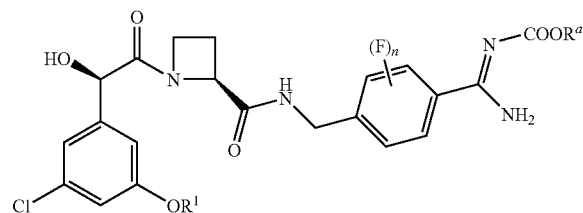

VI wherein R<sup>a</sup> represents, for example, —CH₂CH₂—Si(CH₃)₃ or benzyl, and R¹ and n are as hereinbefore defined, or a tautomer thereof, with a compound of formula VII,

 VII wherein R² is as hereinbefore defined, or an acid addition salt thereof, for example at between room and reflux temperature in the presence of an appropriate organic solvent (e.g. THF, CH₃CN, DMF or DMSO), followed by removal of the —C(O)OR<sup>a</sup> group under conditions known to those skilled in the art (e.g. by reacting with QF or TFA (e.g. as described hereinafter)).

Compounds of formula II are available using known and/or standard techniques.

For example, compounds of formula II may be prepared by reaction of an aldehyde of formula VIII,

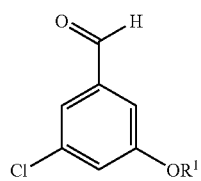

VIII wherein R¹ is as hereinbefore defined with:

(a) a compound of formula IX,

 IX wherein R" represents H or (CH₃)₃Si, for example at room, or elevated, temperature (e.g. below 100° C.) in the presence of a suitable organic solvent (e.g. chloroform or methylene chloride) and, if necessary, in the presence of a suitable base (e.g. TEA) and/or a suitable catalyst system (e.g. benzylammonium chloride or zinc iodide, or using a chiral catalyst, for example as described in *Chem. Rev.*, (1999) 99, 3649), followed by hydrolysis under conditions that are well known to those skilled in the art (e.g. as described hereinafter);

(b) NaCN or KCN, for example in the presence of NaHSO₃ and water, followed by hydrolysis;

(c) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis;

(d) a compound of formula X,

X wherein M represents Mg or Li, followed by oxidative cleavage (e.g. ozonolysis or osmium or ruthenium catalysed) under conditions which are well known to those skilled in the art; or (e) tris(methylthio)methane under conditions which are well known to those skilled in the art, followed by hydrolysis in the presence of e.g. HgO and HBF₄.

Compounds of formula II may alternatively be prepared by oxidation of a compound of formula XI,

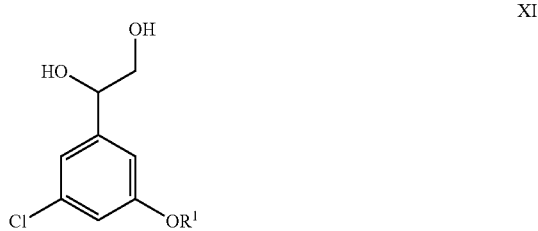

XI or a derivative thereof that is optionally protected at the secondary hydroxyl group, wherein R¹ is as hereinbefore defined, in the presence of a suitable oxidising agent (e.g. a combination of a suitable free radical oxidant (such as TEMPO) and an appropriate hypochlorite salt (such as sodium hypochlorite)) under conditions known to those skilled in the art, for example at between −10° C. and room temperature, in the presence of a suitable solvent (e.g. water, acetone or a mixture thereof), an appropriate salt (e.g. an alkali metal halide such as potassium bromide) and a suitable base (e.g. an alkali metal carbonate or hydrogen carbonate such as sodium hydrogen carbonate).

In the formation of compounds of formula II, the skilled person will appreciate that the required enantiomeric form may be prepared by way of routine enantiomeric separation techniques, for example by an enantiospecific derivatisation step. This may be achieved, for example by an enzymatic process. Such enzymatic processes include, for example, transesterification of the α-OH group at between room and reflux temperature (e.g. at between 45 and 65° C.) in the presence of a suitable enzyme (e.g. Lipase PS Amano), an appropriate ester (e.g. vinyl acetate) and a suitable solvent (e.g. methyl tert-butyl ether). The derivatised isomer may then be separated from the unreacted isomer by conventional separation techniques (e.g. chromatography).

Groups added to compounds of formula U in such a derivatisation step may be removed either before any further reactions or at any later stage in the synthesis of compounds of formula I. The additional groups may be removed using conventional techniques (e.g. for esters of the α-OH group, hydrolysis under conditions known to those skilled in the art (e.g. at between room and reflux temperature in the presence of a suitable base (e.g. NaOH) and an appropriate solvent (e.g. MeOH, water or mixtures thereof))).

Compounds of formula III may be prepared by coupling (S)-azetidine-2-carboxylic acid to a compound of formula V, as hereinbefore defined, for example under similar conditions to those described herein for preparation of compounds of formula I.

Compounds of formula IV may be prepared by coupling a compound of formula II as hereinbefore defined to (S)-azetidine-2-carboxylic acid, for example under similar conditions to those described herein for preparation of compounds of formula I.

Compounds of formula VI may be prepared by reaction of a corresponding compound of formula II, as hereinbefore defined, with a compound of formula XII,

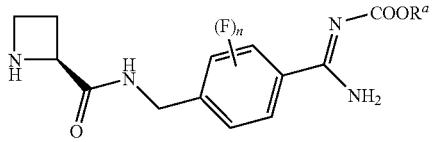

XII wherein n and $R^a$ are as hereinbefore defined, for example under similar conditions to those described hereinbefore for synthesis of compounds of formula I.

Alternatively, compounds of formula VI may be prepared by reaction of a compound corresponding to a compound of formula I, except that, in place of the group —$OR^2$, a H atom is present (i.e. a corresponding free amidine compound), with a compound of formula XIII, $L^1COOR^a$           XIII wherein $L^1$ represents a suitable leaving group, such as halo or nitrophenyl (e.g. 4-nitrophenyl), and $R^a$ is as hereinbefore defined, for example at or around room temperature in the presence of suitable base (e.g. NaOH, for example in aqueous solution) and an appropriate organic solvent (e.g. methylene chloride).

Compounds of formula VIII are available using known and/or standard techniques. For example, they may be prepared by:

(i) metallation (wherein the metal may be, for example, an alkali metal such as Li or, preferably, a divalent metal such as Mg) of a compound of formula XIV,

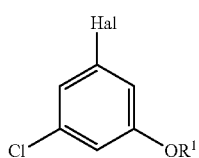

XIV wherein Hal represents a halogen atom selected from Cl, Br and I and $R^1$ is as hereinbefore defined, followed by reaction with a suitable source of the formyl group (such as N,N-dimethylformamide), for example under conditions described hereinafter;

(ii) reduction of a compound of formula XV,

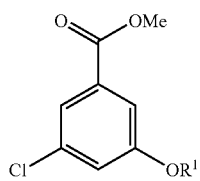

XV wherein $R^1$ is as hereinbefore defined in the presence of a suitable reducing agent (e.g. DIBAL-H); or (iii) oxidation of a compound of formula XVI,

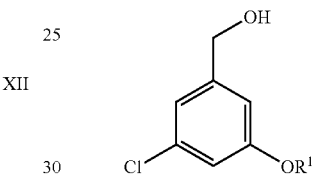

XVI wherein $R^1$ is as hereinbefore defined in the presence of a suitable oxidising agent (e.g. $MnO_2$, pyridinium chlorochromate, a combination of DMSO and oxalyl chloride, or $SO_3$ pyridine complex in DMSO).

Compounds of formula XII may be prepared by reaction of (S)-azetidine-2-carboxylic acid with a compound of formula XVII,

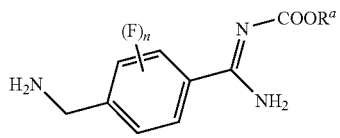

XVII wherein n and $R^a$ are as hereinbefore defined, for example under similar conditions to those described hereinbefore for synthesis of compounds of formula I.

Compounds of formula V, VII, IX, X, XI, XIII, XIV, XV, XVI, XVI and (S)-azetidine-2-carboxylic acid are either commercially available, are known in the literature, or may be obtained either by analogy with the processes described herein, or by conventional synthetic procedures, in accordance with standard techniques, from readily available starting materials using appropriate reagents and reaction conditions, Free amidine equivalents of compounds of formula I may be prepared in analogous fashion to processes described herein for preparation of compounds of formula I.

We have found that certain compounds of the invention have the advantage that they may be prepared in crystalline form.

According to a further aspect of the invention there is provided a compound of the invention in substantially crystalline form.

Although we have found that it is possible to produce compounds of the invention in forms which are greater than 80% crystalline, by "substantially crystalline" we include greater than 20%, preferably greater than 30%, and more preferably greater than 40% (e.g. greater than any of 50, 60, 70, 80 or 90%) crystalline.

According to a further aspect of the invention there is also provided a compound of the invention in partially crystalline form. By "partially crystalline" we include 5% or between 5% and 20% crystalline.

The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

Compounds of the invention, and particularly crystalline compounds of the invention, may have improved stability when compared to compounds disclosed in PCT/SE01/02657.

The term "stability" as defined herein includes chemical stability and solid state stability.

By "chemical stability", we include that it may be possible to store compounds of the invention in an isolated form, or in the form of a formulation in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition.

By "solid state stability", we include that it may be possible to store compounds of the invention in an isolated solid form, or in the form of a solid formulation in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 60%), and/or exposure to 460 lux of UV/visible light, for prolonged periods (i.e. greater than or equal to six months). Under such conditions, compounds of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

Preferred compounds of the invention that may be prepared in crystalline form include salts of $C_{1-6}$ (e.g. $C_{2-6}$, such as $C_{2-4}$) alkanesulfonic acids, such as ethanesulfonic acid, propanesulfonic acid (e.g. n-propanesulfonic acid) and optionally substituted arylsulfonic acids, such as benzenesulfonic acid.

It may be possible to crystallise salts of Compounds A, B and C with or without the presence of a solvent system (e.g. crystallisation may be from a melt, under supercritical conditions, or achieved by sublimation). However, we prefer that crystallisation occurs from an appropriate solvent system.

Appropriate solvent systems that may be used in a crystallisation process may be heterogeneous or homogeneous and may thus comprise one or more organic solvents, such as lower alkyl acetates (e.g. linear or branched $C_{1-6}$ alkyl acetates, such as ethyl acetate, iso-propyl acetate and butyl acetate); lower (e.g. linear or branched $C_{1-6}$) alkyl alcohols, such as hexan-1-ol, 3-methylbutan-1-ol pentan-1-ol, pentan-2-ol, 4-methyl-2-pentanol and 2-methyl-1-propanol, methanol, ethanol, n-propanol, iso-propanol and butanol (e.g. n-butanol); aliphatic hydrocarbons (e.g. linear or branched $C_{5-8}$ alkanes, such as n-pentane, n-heptane and iso-octane); aromatic hydrocarbons (e.g. benzene, toluene, o-xylene, m-xylene and p-xylene); chlorinated alkanes (e.g. chloroform and dichloromethane); dialkyl (e.g. di-$C_{1-6}$ alkyl) ketones (e.g. acetone, methyl iso-butyl ketone), acetonitrile, dimethylformamide, dialkyl ethers (e.g. diethyl ether, di-iso-propyl ether, di-n-propyl ether, di-n-butyl ether and tert-butyl methyl ether); and/or aqueous solvents, such as water. Mixtures of any of the above-mentioned solvents may be used, Different salts may have different solubilities in any given solvent at any given temperature. In this respect, compounds of the invention may be readily soluble in certain solvents (including some of those mentioned above), yet may be less soluble in others. Solvents in which compounds are the invention are poorly soluble may be termed "antisolvents".

Suitable solvents in which compounds of the invention may be readily soluble include lower alkyl alcohols (such as methanol, ethanol and iso-propanol). Lower alkyl acetates (such as ethyl acetate and iso-propyl acetate), lower dialkyl ketones (such as methyl iso-butyl ketone), aliphatic hydrocarbons (such as iso-octane and n-heptane) and aromatic hydrocarbons (such as toluene) may be employed as antisolvents.

Crystallisation of compounds of the invention from an appropriate solvent system may be achieved by attaining supersaturation in a solvent system comprising compound of the invention (e.g. by cooling, by solvent evaporation and/or via the addition of antisolvent).

It is preferred that crystalline compounds of the invention (and particularly crystalline Compounds A, B and C) are provided by one or more of the following methods:

(i) preparation of a compound of the invention in amorphous form, followed by dissolution of that salt in an appropriate solvent system, such as a polar solvent (e.g. a lower alkyl alcohol, a lower alkyl acetate, a lower dialkyl ketone, or a mixture of these solvents), and subsequent crystallisation (optionally initiated by seeding). Crystallisation may be effected in this way by dissolving compound of the invention in a solvent in which it is readily soluble (e.g. a lower alkyl alcohol), followed by addition of antisolvent (e.g. a lower alkyl acetate or a lower di alkyl ketone), or by dissolving compound in a mixture of a solvent in which it is readily soluble and an antisolvent, and subsequent crystallisation; or (ii) reaction crystallisation (or precipitation), which comprises adding an appropriate amount of acid to a compound of formula I, and then either:—

(a) direct crystallisation, for example from a solvent system that comprises an antisolvent (e.g. a lower alkyl acetate, a lower dialkyl ketone or a hydrocarbon); or (b) subsequent addition of an appropriate antisolvent to facilitate crystallisation (e.g. formation of compound of the invention in a solvent in which it is readily soluble (e.g. a lower alkyl alcohol), followed by addition of antisolvent (e.g. an acetate, a lower alkyl ketone or a hydrocarbon)), in both of which processes (a) and (b), acid and/or base may be initially provided in association with the appropriate solvent system, and in both of which processes (a) and (b), crystallisation may be initiated by seeding.

In the case of process (i) above, preferred solvents may include methyl iso-butyl ketone, iso-propanol, ethyl acetate, iso-propyl acetate and mixtures thereof.

In the case of process (ii) above, depending on the salt that is to be formed:

(a) preferred solvents for "direct" crystallisation may include iso-propanol, iso-propyl acetate, n-butyl acetate, toluene or, preferably, methyl iso-butyl ketone or ethyl acetate; and (b) when the crystallisation employs antisolvent, preferred solvents in which compounds of the invention are readily soluble may include methanol, ethanol or, preferably, iso-propanol; and preferred antisolvents may include methyl iso-butyl ketone, n-butyl acetate, toluene, iso-octane, n-heptane or, preferably, ethyl acetate or iso-propyl acetate, In any of processes (i) or (ii), the skilled person will appreciate that, following salt formation, at least part of the solvent (s) may be removed, and then the resultant mixture re-dissolved prior to performing a crystallisation as described herein.

When the crystalline compound of the invention to be formed is an ethanesulfonate salt of Compound A, and:

(1) the process performed is process (i), amorphous salt may be slurried in either methyl iso-butyl ketone or a mixture of iso-propanol and ethyl acetate; and (2) the process performed is process (ii), a direct crystallisation may be achieved by adding ethanesulfonic acid, optionally in the form of a solution in methyl iso-butyl ketone, to a solution of Compound A in methyl iso-butyl ketone. Alternatively, ethanesulfonic acid may be added to a solution of Compound A in iso-propanol, and ethyl acetate may then be added as antisolvent.

When the crystalline compound of the invention to be formed is an n-propanesulfonate salt of Compound A, and:

(I) the process performed is process (i), amorphous salt may be slurried in a mixture of iso-propanol and iso-propyl acetate, or in a mixture of iso-propanol and ethyl acetate; and (II) the process performed is process (ii), n-propanesulfonic acid may be added to a solution of Compound A in iso-propanol and then ethyl acetate, or iso-propyl acetate, added as antisolvent.

When the crystalline compound of the invention to be formed is a benzenesulfonate salt of Compound A, and:

(A) the process performed is process (i), amorphous salt may be slurried in ethyl acetate, methyl iso-butyl ketone or iso-propyl acetate; and (B) the process performed is process (ii), benzenesulfonic acid may be added to a solution of Compound A in ethyl acetate, and then a small amount of iso-propanol added to facilitate transformation into crystalline material. Alternatively, benzenesulfonic acid may be added to a solution of Compound A in iso-propanol, and then ethyl acetate added as antisolvent.

According to a further aspect of the invention, there is provided a process for the preparation of a crystalline compound of the invention which comprises crystallising a compound of the invention from an appropriate solvent system.

Crystallisation temperatures and crystallisation times depend upon the salt that is to be crystallised, the concentration of that salt in solution, and the solvent system which is used.

Crystallisation may also be initiated and/or effected by way of standard techniques, for example with or without seeding with crystals of the appropriate crystalline compound of the invention.

Compounds of the invention that are anhydrates contain no more than 3%, preferably 2%, more preferably 1% and more preferably 0.5% (w/w) water, whether such water is bound (crystal water or otherwise) or not.

Different crystalline forms of the compounds of the invention may be readily characterised using X-ray powder diffraction (XRPD) methods, for example as described hereinafter.

In order to ensure that a particular crystalline form is prepared in the absence of other crystalline forms, crystallisations are preferably carried out by seeding with nuclei and/or seed crystals of the desired crystalline form in substantially complete absence of nuclei and/or seed crystals of other crystalline forms. Seed crystals of appropriate compound may be prepared, for example, by way of slow evaporation of solvent from a portion of solution of appropriate salt.

Compounds of the invention may be isolated using techniques which are well known to those skilled in the art, for example decanting, filtering or centrifuging.

Compounds may be dried using standard techniques.

Further purification of compounds of the invention may be effected using techniques, which are well known to those skilled in the art. For example impurities may be removed by way of recrystallisation from an appropriate solvent system. Suitable temperatures and times for the recrystallisation depend upon the concentration of the salt in solution, and upon the solvent system which is used.

When compounds of the invention are crystallised, or recrystallised, as described herein, the resultant salt may be in a form which has improved chemical and/or solid state stability, as mentioned hereinbefore.

Pharmaceutical Preparations and Medical Uses

Compounds of the invention may be administered parenterally or orally to mammalian patients (including humans), and may thereafter be metabolised in the body to form compounds that are pharmacologically active (i.e. they act as "prodrugs" of active compounds).

Thus, the compounds of the invention are useful because they are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are metabolised following administration to form potent inhibitors of thrombin, for example as may be demonstrated in the tests described in inter alia international patent application No. PCT/SE01/02657, as well as international patent applications WO 02/14270, WO 01/87879 and WO 00/42059, the relevant disclosures in which documents are hereby incorporated by reference.

By "prodrug of a thrombin inhibitor", we include compounds that form a thrombin inhibitor, in an experimentally-detectable amount, and within a predetermined time (e.g. about 1 hour), following oral or parenteral administration.

The compounds of the invention are thus expected to be useful in those conditions where inhibition of thrombin is required, and/or conditions where anticoagulant therapy is indicated, including the following:

The treatment and/or prophylaxis of thrombosis and hypercoaguability in blood and/or tissues of animals including man. It is known that hypercoaguability may lead to thrombo-embolic diseases. Conditions associated with hypercoaguability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoaguability and thrombo-embolic disease include circulating antiphospholipid antibodies (Lupus anticoagulant), homocysteinemi, heparin induced thrombocytopenia and defects in fibrinolysis, as well as coagulation syndromes (e.g. disseminated intravascular coagulation (DIC)) and vascular injury in general (e.g. due to surgery).

The treatment of conditions where there is an undesirable excess of thrombin without signs of hypercoaguability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation (e.g. non-valvular atrial fibrillation) or from the left ventricle after transmural myocardial infarction, or caused by congestive heart failure; prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in hemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

Compounds of the invention that inhibit trypsin and/or thrombin may also be useful in the treatment of pancreatitis.

The compounds of the invention are thus indicated both in the therapeutic and/or prophylactic treatment of these conditions.

According to a further aspect of the present invention, there is provided a method of treatment of a condition where inhibition of thrombin is required which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally tracheally, bronchially, by any other parenteral route or via inhalation, in the form of pharmaceutical preparations comprising compound of the invention in a pharmaceutically acceptable dosage form.

Depending upon the disorder and patient to be treated and the route of administration, the compositions may be administered at varying doses.

The compounds of the invention may also be combined and/or co-administered with any antithrombotic agent(s) with a different mechanism of action, such as one or more of the following: the antiplatelet agents acetylsalicylic acid, ticlopidine and clopidogrel; thromboxane receptor and/or synthetase inhibitors; fibrinogen receptor antagonists; prostacyclin mimetics; phosphodiesterase inhibitors; ADP-receptor ($P_2T$) antagonists; and inhibitors of carboxypeptidase U (CPU), The compounds of the invention may further be combined and/or co-administered with thrombolytics such as one or more of tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is provided a pharmaceutical formulation including a compound of the invention, in admixture with a pharmaceutically acceptable adjuvant, diluent or carrier.

Suitable daily doses of the compounds of the invention in therapeutic treatment of humans are about 0.001-100 mg/kg body weight at peroral administration and 0.001-50 mg/kg body weight at parenteral administration, excluding the weight of any acid counter-ion.

For the avoidance of doubt, as used herein, the term "treatment" includes therapeutic and/or prophylactic treatment.

Compounds of the invention have the advantage that they may be more efficacious, be less toxic, be longer acting, have a broader range of activity, be more potent, produce fewer side effects, be more easily absorbed, and/or have a better pharmacokinetic profile (e.g. higher oral bioavailability and/or lower clearance), than, and/or have other useful pharmacological, physical, or chemical, properties over, compounds known in the prior art. Compounds of the invention may have the further advantage that they may be administered less frequently than compounds known in the prior art.

Compounds of the invention may also have the advantage that they are in a form which provides for improved ease of handling. Further, compounds of the invention have the advantage that they may be produced in forms which may have improved chemical and/or solid state stability (including e.g. due to lower hygroscopicity). Thus, such compounds of the invention may be stable when stored over prolonged periods.

Compounds of the invention may also have the advantage that they may be crystallised in good yields, in a high purity, rapidly, conveniently, and at a low cost.

The invention is illustrated, but in no way limited, by the following examples, with reference to the enclosed figures in which.

GENERAL PROCEDURES

Figure 1:
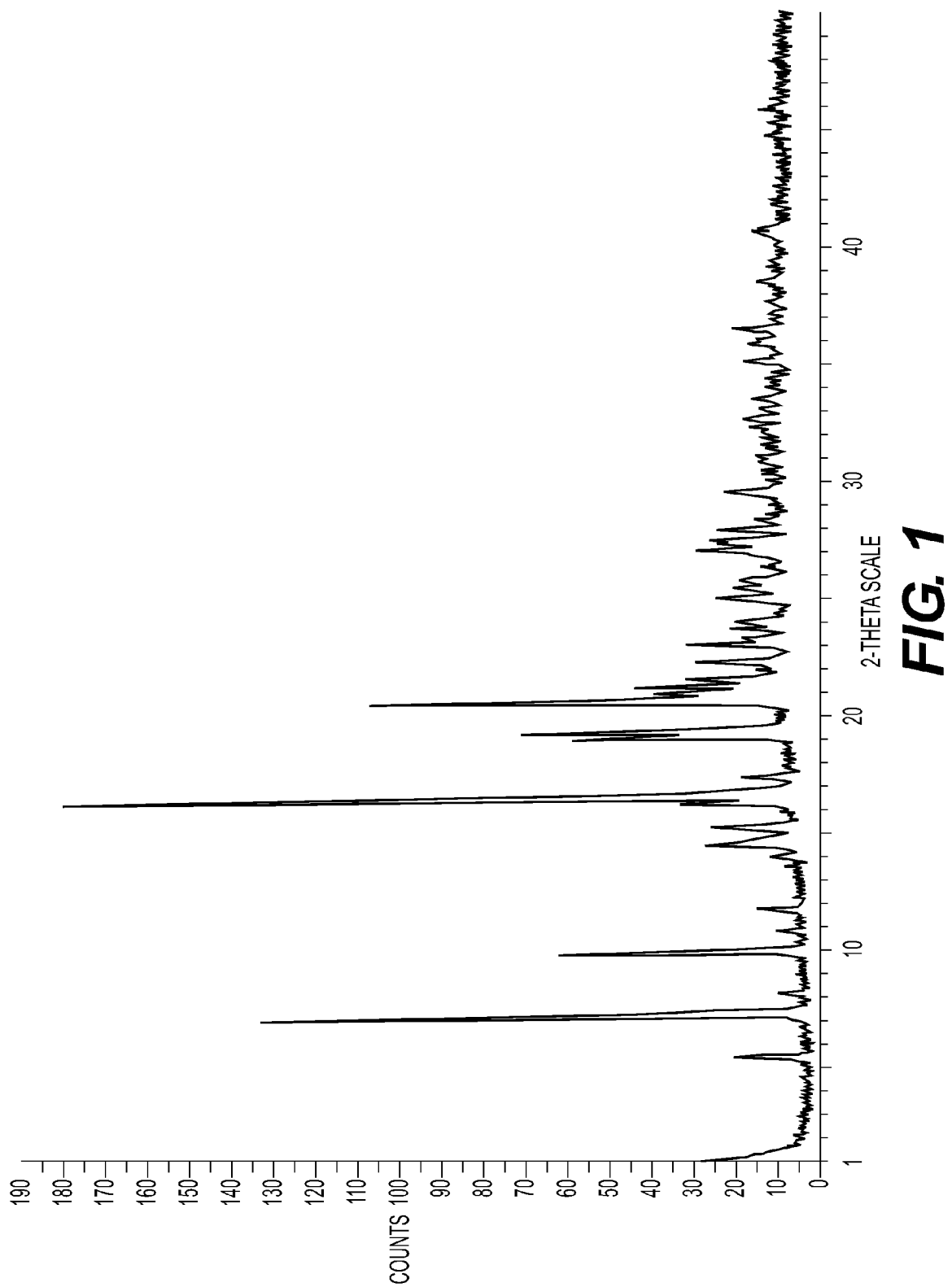
FIG. 1 shows an X-ray powder diffractogram for crystalline Compound A, ethanesulfonic acid salt.

TLC was performed on silica gel. Chiral HPLC analysis was performed using a 46 mm×250 mm Chiralcel OD column with a 5 cm guard column. The column temperature was maintained at 35° C. A flow rate of 1.0 mL/min was used. A Gilson 115 UV detector at 228 nm was used. The mobile phase consisted of hexanes, ethanol and trifluoroacetic acid and the appropriate ratios are listed for each compound. Typically, the product was dissolved in a minimal amount of ethanol and this was diluted with the mobile phase.

In Preparations A to C below, LC-MSM/S was performed using a HP-1100 instrument equipped with a CTC-PAL injector and a 5 Tm, 4×100 mm ThermoQuest, Hypersil BDS-C18 column. An API-3000 (Sciek) MS detector was used. The flow rate was 1.2 mL/min and the mobile phase (gradient) consisted of 10-90% acetonitrile with 90-10% of 4 mM aq. ammonium acetate, both containing 0.2% formic acid. Otherwise, low resolution mass spectra (LRMS) were recorded using a Micromass ZQ spectrometer in ESI posneg switching ion mode (mass range m/z 100-800); and high resolution mass spectra (HRMS) were recorded using a Micromass LCT spectrometer in ES negative ionization mode (mass range m/z 100-1000) with Leucine Enkephalin ($C_{28}H_{37}N_5O_7$) as internal mass standard.

$^1$H NMR spectra were recorded using tetramethylsilane as the internal standard. $^{13}$C NMR spectra were recorded using the listed deuterated solvents as the internal standard. Otherwise, MeOD was used as solvent and the MeOD signal as internal standard ($^1$H Λ=3.30 ppm; $^{13}$C Λ=49 ppm).

X-ray powder diffraction analysis (XRPD) was performed using variable slits on samples prepared according to standard methods with and without using any internal standard, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendoni Press, London; or Klug, H. P. & Alexander, L. E. (1974), *X-ray Diffraction Procedures*, John Wiley and Sons, New York. X-ray analyses were performed using a Siemens D5000 diffractometer and a Philips X'Pert MPD.

Differential scanning calorimetry (DSC) was performed using a Mettler DSC820 instrument, according to standard methods, for example those described in Höhne, G. W. H. et al (1996), *Differential Scanning Calorimetry*, Springer, Berlin.

Thermogravimetric analysis (TGA) was performed using a Mettler Toledo TGA850 instrument.

It will be appreciated by the skilled person that crystalline forms of compounds of the invention may be prepared by analogy with processes described herein and/or in accordance with the Examples below, and may show essentially the same XRPD diffraction patterns and/or DSC and/or TGA thermograms as those disclosed herein. By "essentially the same" XRPD diffraction patterns and/or DSC and/or TGA thermograms, we include those instances when it is clear from the relevant patterns and/or thermograms (allowing for experimental error) that essentially the same crystalline form has been formed. When provided, DSC onset temperatures may vary in the range ±5° C. (e.g. ±2° C.), and XRPD distance values may vary in the range ±2° on the last decimal place. It will be appreciated by the skilled person that XRPD intensities may vary when measured for essentially the same crystalline form for a variety of reasons including, for example, preferred orientation.

The intensity of XRPD data is generally within a margin of error of approximately plus or minus 20 to 40%. The relative intensities may be characterised according to the following definitions:—

| % Relative Intensity | Definition |
| --- | --- |
| 60-100 | vs (very strong) |
| 21-59.9 | s (strong) |
| 7-20.9 | m (medium) |
| 4-6.9 | w (weak) |
| <1-3.9 | vw (very weak) |

In the Examples section, unless stated otherwise, when seeding is performed the seeds are obtained from the first Example in which crystalline material of that salt is obtained. For example, in Example 13, seeds are obtained from Example 11.

Preparation A

Preparation of Compound A (i) 3-Chloro-5-methoxybenzaldehyde 3,5-Dichloroanisole (74.0 g, 419 mmol) in THF (200 ml) was added dropwise to magnesium metal (14.2 g, 585 mmol, pre-washed with 0.5 N HCl) in THF (100 mL) at 25° C. After the addition, 1,2-dibromoethane (3.9 g, 20.8 mmol) was added dropwise. The resultant dark brown mixture was heated at reflux for 3 h. The mixture was cooled to 0° C., and N,N-dimethylformamide (60 mL) was added in one portion. The mixture was partitioned with diethyl ether (3×400 µL) and 6N HCl (500 mL). The combined organic extracts were washed with brine (300 mL), dried ($Na_2SO_4$), filtered and concentrated in vacuo to give an oil. Flash chromatography (2×) on silica gel eluting with Hex:EtOAc (4:1) afforded the sub-title compound (38.9 g, 54%) as a yellow oil.

$^1$H NMR (300 MHz, CDCl$_3$) δ 9.90 (s, 1H), 7.53 (s, 1H), 7.38 (s, 1H, 7.15 (s, 1H), 3.87 (s, 3H).

(ii) 3-Chloro-5-hydroxybenzaldehyde

A solution of 3-chloro-5-methoxybenzaldehyde (22.8 g, 134 mmol; see step (i) above) in CH$_2$Cl$_2$ (250 µL) was cooled to 0° C. Boron tribromide (15.8 mL, 167 mmol) was added dropwise over 15 min. After stirring, the reaction mixture for 2 h, H$_2$O (50 mL) was added slowly. The solution was then extracted with Et$_2$O (2×100 mL). The organic layers were combined, dried (Na$_2$SO$_4$), filtered and concentrated in vacuo. Flash chromatography on silica gel eluting with Hex: EtOAc (4:1) afforded the sub-title compound (5.2 g, 25%).

$^1$H NMR (300 MHz, CDCl$_3$) δ 9.85 (s, 1H), 7.35 (s, 1H), 7.20 (s, 1H), 7.10 (s, 1H), 3.68 (s, 1H)

(iii) 3-Chloro-5-difluoromethoxybenzaldehyde

A solution of 3-chloro-5-hydroxybenzaldehyde (7.5 g, 48 mmol; see step (ii) above) in 2-propanol (250 mL) and 30% KOH (100 mL) was heated to reflux. While stirring, CHClF$_2$ was bubbled into the reaction mixture for 2 h. The reaction mixture was cooled, acidified with 1N HCl and extracted with EtOAc (2×100 mL). The organics were washed with brine (100 mL), dried (Na$_2$SO$_4$), filtered and concentrated in vacuo. Flash chromatography on silica gel eluting with Hex:EtOAc (4:1) afforded the sub-title compound (4.6 g, 46%).

$^1$H NMR (300, MHz, CDCl$_3$) δ 9.95 (S, 1H), 7.72 (s, 1H), 7.52 (s, 1H), 7.40 (s, 1H), 6.60 (t, J$_{H-F}$=71.1 Hz, 1H)

(iv) Ph(3-Cl)(5-OCHF$_2$))—(R,S)CH(OTMS)CN

A solution of 3-chloro-5-difluorormethoxybenzaldehyde (4.6 g, 22.3 mmol; see step (iii) above) in CH$_2$Cl$_2$ (200 mL) was cooled to 0° C. ZnI$_2$ (1.8 g, 5.6 mmol) and trimethylsilyl cyanide (2.8 g, 27.9 mmol) were added and the reaction mixture was allowed to warm to room temperature and stirred for 15 h. The mixture was partially concentrated in vacuo yielding the sub-title compound as a liquid, which was used directly in step (v) below without further purification or characterization.

(v) Ph(3-Cl)(5-OCHF$_2$)—(R,S)CH(OH)C(NH)OEt

Ph(3-Cl)(5-OCHF$_2$)—(R,S)CH(OTMS)CN (6.82 g, assume 22.3 mmol; see step (iv) above) was added dropwise to HCl/EtOH (500 mL). The reaction mixture was stirred 15 h, then partially concentrated in vacuo yielding the sub-title compound as a liquid, which was used in step (vi) without further purification or characterization.

(vi) Ph(3-Cl)(5-OCHF$_2$)—(R,S)CH(OH)C(O)OEt

Ph(3-Cl)(5-OCHF$_2$)—(R,S)CH(OH)C(NH)OEt (6.24 g, assume 22.3 mmol; see step (v) above) was dissolved in THF (250 μL), 0.5M H$_2$SO$_4$ (400 mL) was added and the reaction was stirred at 40° C. for 65 h, cooled and then partially concentrated in vacuo to remove most of the THF. The reaction mixture was then extracted with Et$_2$O (3×100 mL), dried (Na$_2$SO$_4$), filtered and concentrated in vacuo to afford the sub-title compound as a solid, which was used in step (vii) without further purification or characterization.

(vii) Ph(3-Cl)(5-OCHF$_7$)—(R,S)CH(OH)C(O)OH

A solution of Ph(3-Cl)(5-OCHF$_2$)—(R,S)CH(OH)C(O)OEt (6.25 g, assume 22.3 mmol; see step (vi) above) in 2-propanol (175 μL) and 20% KOH (350 mL) was stirred at room temperature 15 h. The reaction was then partially concentrated in vacuo to remove most of the 2-propanol. The remaining mixture was acidified with 1M H$_2$SO$_4$, extracted with Et$_2$O (3×100 mL), dried (Na$_2$SO$_4$) and concentrated in vacuo to give a solid. Flash chromatography on silica gel eluting with CHCl$_3$:MeOH:concentrated NH$_4$OH (6:3:1) afforded the ammonium salt of the sub-title compound. The ammonium salt was then dissolved in a mixture of EtOAc (75 at) and H$_2$O (75 mL) and acidified with 2N HCl. The organic layer was separated and washed with brine (50 mL), dried (Na$_2$SO$_4$) and concentrated in vacuo to afford the sub-title compound (3.2 g, 57% from steps (iv) to (vii)).

$^1$H NMR (300 MHz, CD$_3$OD) δ 7.38 (S, 1H), 7.22 (s, 1H), 7.15 (s, 1H), 6.89 (t, J$_{H-F}$=71.1. Hz, 1H), 5.16 (s, 1H)

(viii) Ph(3-Cl)(5-OCHF$_2$)—(R)CH(OH)C(O)OH (a) and Ph(3-Cl)(5-OCHF$_2$)—(S)CH(OAc)C(CO)OH (b)

A mixture of Ph(3-Cl)(5-OCHF$_2$)—(R,S)CH(OH)C(O)OH (3.2 g, 12.7 mmol; see step (vii) above) and Lipase PS "Amano" (~2.0 g) in vinyl acetate (125 mL) and MTBE (125 mL) was heated at reflux for 48 h. The reaction mixture was cooled, so filtered through Celite® and the filter cake washed with EtOAc. The filtrate was concentrated in vacuo and subjected to flash chromatography on silica gel eluting with CHCl$_3$:MeOH:concentrated NH$_4$OH (6:3:1) yielding the ammonium salts of the sub-title compounds (a) and (b). Compound (a) as a salt was dissolved in H$_2$O, acidified with 2N HCl and extracted with EtOAc. The organic layer was washed with brine, dried (Na$_2$SO$_4$), filtered and concentrated in vacuo to afford the sub-title compound (a) (1.2 g, 37%).

For Sub-Title Compound (A)

$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.1 (s, 1H)

(ix) Ph(3-Cl)(5-OCHF$_2$)—R)CH(OH)C(O)-Aze-Pab (Teoc)

To a solution of Ph(3-Cl)(5-OCHF$_2$)—(R)CH(OH)C(O) OH (1.1 g, 4.4 mmol; see step (viii) above) and H-Aze-Pab (Teoc) (see international patent application WO 00/42059, 2.6 g, 5.7 mmol) in DMF (50 mL) at 0° C. was added PyBOP (2.8 g, 5.3 mmol) and collidine (1.3 g, 10.6 mmol). The reaction was stirred at 0° C. for 2 h and then at room temperature for an additional 15 h. The reaction mixture was concentrated in vacuo and flash chromatographed on silica gel (3×), eluting first with CHCl$_3$:EtOH (9:1), then with EtOAc:EtOH (20:1) and finally eluting with CH$_7$Cl$_2$:CH$_3$OH (95:5) to afford the sub-title compound (1.0 g, 37%) as a white amorphous solid.

$^1$H NMR (300 MHz, CD$_3$OD, mixture of rotamers) δ 7.79-7.85 (d, J=8.7 Hz, 2H), 7.15-7.48 (m, 5H), 6.89 and 6.91 (t, J$_{H-F}$=71.1 Hz, 1H), 5.12 and 5.20 (s, 1H), 4.75-4.85 (m, 1H), 3.97-4.55 (m, 6H), 2.10-2.75 (m, 2H), 1.05-1.15 (m, 2H), 0.09 (s, 9H)

MS (m/z) 611 (M+1)$^+$ (x) Ph(3-Cl)(5-OCHF$_2$)—(R)CH(OH)C(O)-Aze-Pab (OMe, Teoc)

Ph(3-Cl)(5-OCHF$_2$)—(R)CH(OH)C(O)-Aze-Pab(Teoc) (0.40 g, 0.65 mmol, see step (ix) above), was dissolved in 20 mL of acetonitrile and 0.50 g (6.0 mmol) of O-methyl hydroxylamine hydrochloride was added. The mixture was heated at 70° C. for 2 h. The solvent was evaporated and the residue was partitioned between water and ethyl acetate. The aqueous phase was extracted twice more with ethyl acetate and the combined organic phase was washed with water, brine, dried (Na$_2$SO$_4$), filtered and evaporated. Yield: 0.41 g (91%).

$^1$H-NMR (400 MHz; CDCl$_3$): δ 7.83 (bt, 1H), 7.57 (bs, 1H), 7.47 (d, 2H), 7.30 (d, 2H), 7.20 (m, 1H), 7.14 (m, 1H), 7.01 (m, 1H), 6.53 (t, 1H), 4.89 (s, 1H), 4.87 (m, 1H), 4.47 (m, 2H), 4.4-4.2 b, 1H), 4.17-4.1 (m, 3H), 3.95 (s, 3H), 3.67 (m, 1H), 2.68 (m, 1H), 2.42 (m, 1H) 0.97 (m, 2H), 0.01 (s, 9H).

(xi) Compound A

Ph(3-Cl)(5-OCHF$_2$)—(R)CH(ON)C(O)-Aze-Pab(OMe, Teoc) (0.40 g, 0.62 mmol; see step (x) above) was dissolved in 5 mL of TFA and allowed to react for 30 min. TFA was evaporated and the residue was partitioned between ethyl acetate and NaHCO$_3$ (aq.). The aqueous phase was extracted twice more with ethyl acetate and the combined organic phase was washed with water, brine, dried (Na$_2$SO$_4$), filtered and evaporated. The product was freeze dried from water/acetonitrile. No purification was necessary. Yield: 0.28 g (85%).

$^1$H-NMR (600 MHz; CDCl$_3$): δ 7.89 (bt, 1H), 7.57 (d, 2H), 7.28 (d, 2H), 7.18 (m, 1H), 7.13 (m, 1H), 6.99 (m, 1H), 6.51 (t, 1H), 4.88 (s, 1H), 4.87 (m, 1H), 4.80 (bs, 2H), 4.48 (dd, 1H), 4.43 (dd, 1H), 4.10 (m, 1H), 3.89 (s, 3H), 3.68 (m, 1H), 2.68 (m, 1H), 2.40 (m, 1H).

$^{13}$C-NMR (125 MHz; CDCl$_3$): (carbonyl and/or amidine carbons, rotamers) δ 172.9, 170.8, 152.7, 152.6

HRMS calculated for C$_{22}$H$_{23}$ClF$_2$N$_4$O$_5$ (M-H)$^-$ 495.1242, found 495.1247

Preparation B

Preparation of Compound B (i) 2,6-Difluoro-4[(methylsulfinyl)(methylthio)methyl]benzonitrile (Methylsulfinyl)(methylthio)methane (7.26 g, 0.0584 mol) was dissolved in 100 mL of dry THF under argon and was cooled to −78° C. Butyllithium in hexane (16 mL 1.6M, 0.0256 mol) was added dropwise with stirring. The mixture was stirred for 15 min. Meanwhile, a solution of 3,4,5-trifluorobenzonitrile (4.0 g, 0.025 mmol) in 100 mL of dry TAP was cooled to 78° C. under argon and the former solution was added through a cannula to the latter solution over a period of 35 min. After 30 min, the cooling bath was removed and when the reaction had reached room temperature it was poured into 400 mL of water. The TAP was evaporated and the remaining aqueous layer was extracted three times with diethyl ether. The combined ether phase was washed with water, dried (Na$_2$SO$_4$) and evaporated. Yield: 2.0 g (30%).

$^1$H NMR (500 MHz, CDCl$_3$) δ 7.4-7.25 (m, 2N), 5.01 (s, 1H, diasteromer), 4.91 (s, 1H, diasteromer), 2.88 (s, 31, diasteromer), 2.52 (s, 3H, diasteromer), 2.49 (s, 3H, diasteromer), 2.34 (s, 3H, diasteromer), 1.72 (broad, 1H)

(ii) 2,6-Difluoro-4-formylbenzonitrile 2,6-Difluoro-4[(methylsulfinyl)(methylthio)methyl]benzonitrile (2.17 g, 8.32 mmol; see step (i) above) was dissolved in 90 mL of THF and 3.5 mL of concentrated sulfuric acid was added. The mixture was left at room temperature for 3 days and subsequently poured into 450 mL of water. Extraction three times with EtOAc followed and the combined ethereal phase was washed twice with aqueous sodium bicarbonate and with brine, dried (Na$_2$SO$_4$) and evaporated. Yield: 1.36 g (98%). The position of the formyl group was established by $^{13}$C NMR. The signal from the fluorinated carbons at 162.7 ppm exhibited the expected coupling pattern with two coupling constants in the order of 260 Hz and 6.3 Hz respectively corresponding to an ipso and a meta coupling from the fluorine atoms.

$^1$H NMR (400 MHz, CDCl$_3$) δ 10.35 (s, 1H), 7.33 (m, 2H)

(iii) 2,6-Difluoro-4-hydroxymethylbenzonitrile 2,6-Difluoro-4-formylbenzonitrile (1.36 g, 8.13 mmol; see step (ii) above) was dissolved in 25 mL of methanol and cooled on an ice bath, Sodium borohydride (0.307 g, 8.12 mmol) was added in portions with stirring and the reaction was left for 65 min. The solvent was evaporated and the residue was partitioned between diethyl ether and aqueous sodium bicarbonate. The ethereal layer was washed with more aqueous sodium bicarbonate and brine, dried (Na$_2$SO$_4$) and evaporated. The crude product crystallised soon and could be used without further purification. Yield: 1.24 g (90%).

$^1$H NMR (400 MHz, CDCl$_3$) δ 7.24 (m, 2H), 4.81 (s, 2H), 2.10 (broad, 1H)

(iv) 4-Cyano-2,6-difluorobenzyl Methanesulfonate

To an ice cooled solution of 2,6-difluoro-4-hydroxymethylbenzonitrile (1.24 g, 7.32 mmol; see step (iii) above) and methanesulfonyl chloride (0.93 g, 8.1 mmol) in 60 mL of methylene chloride was added triethylamine (0.81 g, 8.1 mmol) with stirring. After 3 h at 0° C., the mixture was washed twice with 1M HCl and once with water, dried (Na$_2$SO$_4$) and evaporated. The product could be used without further purification. Yield: 1.61 g (89%).

$^1$H NMR (300 MHz, CDCl$_3$) δ 7.29 (m, 2H), 5.33 (s, 2H), 3.07 (s, 3H)

(v) 4-Azidomethyl-2,6-difluorobenzonitrile

A mixture of 4-cyano-2,6-difluorobenzyl methanesulfonate (1.61 g, 6.51 mmol, see step (iv) above) and sodium azide (0.72 g, 0.0111 mol) in 10 ml of water and 20 mL of DMF was stirred at room temperature overnight. The resultant was subsequently poured into 200 mL of water and extracted three times with diethyl ether. The combined ethereal phase was washed five times with water, dried (Na$_2$SO$_4$) and evaporated. A small sample was evaporated for NMR purposes and the product crystallised. The rest was evaporated cautiously but not until complete dryness. Yield (theoretically 1.26 g) was assumed to be almost quantitative based on NMR and analytical HPLC.

$^1$H NMR (400 MHz, CDCl$_3$) δ 7.29 (m, 2H), 4.46 (s, 2H)

(vi) 4-Aminomethyl-2,6-difluorobenzonitrile

This reaction was carried out according to the procedure described in *J. Chem. Res.* (M) (1992) 3128. To a suspension of 520 mg of 10% Pd/C (50% moisture) in 20 mL of water was added a solution of sodium borohydride (0.834 g, 0.0221 mol) in 20 mL of water. Some gas evolution resulted. 4-Azidomethyl-2,6-difluorobenzonitrile (1.26 g, 6.49 mmol; see step (v) above) was dissolved in 50 mL of TH-F and added to the aqueous mixture on an ice bath over 15 min. The mixture was stirred for 4 h, whereafter 20 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried (Na$_2$SO$_4$) and evaporated. Yield: 0.87 g (80%).

$^1$H NMR (400 MHz, CDCl$_3$) δ 7.20 (m, 2H), 3.96 (s, 2H), 1.51 (broad, 2H)

(vii) 2,6-Difluoro-4-tert-butoxycarbonylaminomethylbenzonitrile

A solution of 4-aminomethyl-2,6-difluorobenzonitrile (0.876 g, 5.21 mmol; see step (vi) above) was dissolved in 50 mL of THF and di-tert-butyl dicarbonate (1.14 g, 5.22 mmol) in 10 mL of THF was added. The mixture was stirred for 3.5 h. The THF was evaporated and the residue was partitioned between water and EtOAc. The organic layer was washed three times with 0.5 M HCl and water, dried (Na$_2$SO$_4$) and evaporated. The product could be used without further purification. Yield: 1.38 g (99%).

$^1$H NMR (300 MHz, CDCl$_3$) δ 7.21 (m, 2H), 4.95 (broad, 1H), 4.43 (broad, 2H), 1.52 (s, 9H)

(viii) Boc-Pab(2,6-diF)(OH)

A mixture of 2,6-difluoro-4-tert-butoxycarbonylaminomethylbenzonitrile (1.38 g, 5.16 mmol; see step (vii) above), hydroxylamine hydrochloride (1.08 g, 0.0155 mol) and triethylamine (1.57 g, 0.0155 mol) in 20 mL of ethanol was stirred at room temperature for 36 h. The solvent was evaporated and the residue was partitioned between water and methylene chloride. The organic layer was washed with water, dried ($Na_2SO_4$) and evaporated. The product could be used without further purification. Yield: 1.43 g (92%).

$^1$H NMR (500 MHz, $CD_3OD$) δ 7.14 (m, 2H), 4.97 (broad, 1H), 4.84 (broad, 2H), 4.40 (broad, 2H), 1.43 (s, 9H)

(ix) Boc-Pab(2,6-diF) x HOAc

This reaction was carried out according to the procedure described by Judkins et al, *Synth. Comm.* (1998) 4351. Boc-Pab(2,6-diF)(OH) (1.32 g, 4.37 mmol; see step (viii) above), acetic anhydride (0.477 g, 4.68 mmol) and 442 mg of 10% Pd/C (50% moisture) in 100 nm of acetic acid was hydrogenated at 5 atm pressure for 3.5 h. The mixture was filtered through Celite, rinsed with ethanol and evaporated. The residue was freeze-dried from acetonitrile and water and a few drops of ethanol. The sub-title product could be used without further purification. Yield: 1.49 g (99%), $^1$H NMR (400 MHz, $CD_3OD$) δ 7.45 (m, 2H), 4.34 (s, 2H), 1.90 (s, 3H), 1.40 (s, 9H)

(x) Boc-Pab(2,6-diF)(Teoc)

To a solution of Boc-Pab(2,6-diF) x HOAc (1.56 g, 5.49 mmol; see step (ix) above) in 100 mL of THF and 1 mL of water was added 2-(trimethylsilyl)ethyl p-nitrophenyl carbonate (1.67 g, 5.89 mmol). A solution of potassium carbonate (1.57 g, 0.0114 mol) in 20 mL of water was added dropwise over 5 min. The mixture was stirred overnight. The THF was evaporated and the residue was partitioned between water and methylene chloride. The aqueous layer was extracted with methylene chloride and the combined organic phase was washed twice with aqueous sodium bicarbonate, dried ($Na_2SO_4$) and evaporated. Flash chromatography on silica gel with heptane/EtOAc=2/1 gave 1.71 g (73%) of pure compound.

$^1$H NMR (400 MHz, $CDCl_3$) δ 7.43 (m, 2H), 4.97 (broad, 1H), 4.41 (broad, 2H), 4.24 (m, 2H), 1.41 (s, 9H), 1.11 (m, 2H) 0.06 (s, 9H)

(xi) Boc-Aze-Pab(2,6-diF)(Teoc)

Boc-Pab(2,6-diF)(Teoc) (1.009 g, 2.35 mmol; see step (x) above) was dissolved in 50 mL of EtOAc saturated with HCl(g). The mixture was left for 10 min., evaporated and dissolved in 18 mL of DMF, and then cooled on an ice bath. Boc-Aze-OH (0.450 g, 2.24 mmol), PyBOP (1.24 g, 2.35 mmol) and lastly diisopropylethyl amine (1.158 g, 8.96 mmol) were added. The reaction mixture was stirred for 2 h and then poured into 350 mL of water and extracted three times with EtOAc. The combined organic phase was washed with brine, dried ($Na_2SO_4$) and evaporated. Flash chromatography on silica gel with heptane:EtOAc (1:3) gave 1.097 g (96%) of the desired compound.

$^1$H NMR (500 MHz, $CDCl_3$) δ 7.46 (m, 2H), 4.65-4.5 (m, 3H), 4.23 (m, 2H), 3.87 (m, 1H), 3.74 (m, 1H), 2.45-2.3 (m, 2H), 1.40 (s, 9H), 1.10 (m, 2H), 0.05 (s, 9H)

(xii) Ph(3-Cl)(5-OCHF$_2$)—(R)CH(OH)C(O)-Aze-Pab(2,6-diF)(Teoc)

Boc-Aze-Pab(2,6-diF)(Teoc) (0.256 g, 0.500 mmol; see step (xi) above) was dissolved in 20 mL of EtOAc saturated with HCl(g). The mixture was left for 10 min. and evaporated and dissolved in 5 mL of DMF. Ph(3-Cl)(5-OCHF$_2$)—(R)CH(OH)C(O)OH (0.120 g, 0.475 mmol; see Preparation A (viii) above), PyBOP (0.263 g, 0.498 mmol) and lastly diisopropylethyl amine (0.245 g, 1.89 mmol) were added. The reaction mixture was stirred for 2 h and then poured into 350 mL of water and extracted three times with EtOAc. The combined organic phase was washed with brine, dried ($Na_2SO_4$) and evaporated. Flash chromatography on silica gel with EtOAc gave 0.184 (60%) of the desired sub-title compound.

$^1$H NMR (400 MHz, $CD_3OD$, mixture of rotamers) δ 7.55-7.45 (m, 2H), 7.32 (m, 1H, major rotamer), 7.27 (m, 1H, minor rotamer), 7.2-7.1 (m, 2H), 6.90 (t, 1H, major rotamer), 6.86 (t, 1H, minor rotamer), 5.15 (s, 1H, major rotamer), 5.12 (m, 1H, minor rotamer), 5.06 (s, 1H, minor rotamer), 4.72 (m, 1H, major rotamer), 4.6-4.45 (m, 2H), 4.30 (m, 1H, major rotamer), 4.24 (m, 2H), 4.13 (m, 1H, major rotamer), 4.04 (m, 111, minor rotamer), 3.95 (m, 1H, minor rotamer), 2.62 (m, 1H, minor rotamer), 2.48 (m, 1H, major rotamer), 2.22 (m, 1H, major rotamer), 2.10 (m, 1H, minor rotamer), 1.07 (m, 2H), 0.07 (m, 9H)

(xiii) Ph(3-Cl)(5-OCHF$_2$)—(R)CH(OH)C(O)-Aze-Pab(2,6-diF)(OMe,Teoc)

A mixture of Ph(3-Cl)(5-OCHF$_2$)—(R)CH(OH)C(O)-Aze-Pab(2,6-diF)(Teoc) (64 mg, 0.099 mmol; see step (xii) above) and O-methyl hydroxylamine hydrochloride (50 mg, 0.60 mmol) in 4 mL of acetonitrile was heated at 70° C. for 3 h. The solvent was evaporated and the residue was partitioned between water and EtOAc. The aqueous layer was extracted twice with EtOAc and the combined organic phase was washed with water, dried ($Na_2SO_4$) and evaporated. The product could be used without further purification. Yield: 58 mg (87%).

$^1$H NMR (400 MHz, $CDCl_3$) δ 7.90 (bt, 1H), 7.46 (m, 1), 7.25-6.95 (m, 5H), 6.51, t, 1H), 4.88 (s, 1H), 4.83 (m, 1H), 4.6-4.5 (m, 2H), 4.4-3.9 (m, 4H), 3.95 (s, 3H), 3.63 (m, 1H), 2.67 (m, 1H), 2.38 (m, 1H), 1.87 (broad, 1H), 0.98 (m, 2H), 0.01, s, 9H)

(xiv) Compound B

Ph(3-Cl)(5-OCHF$_2$)—(R)CH(OH)C(O)-Aze-Pab(2,6-diF)(OMe,Teoc) (58 mg, 0.086 mmol; see step (xiii) above) was dissolved in 3 mL of TFA, cooled on an ice bath and allowed to react for 2 h. The TFA was evaporated and the residue dissolved in EtOAc. The organic layer was washed twice with aqueous sodium carbonate and water, dried ($Na_2SO_4$) and evaporated. The residue was freeze-dried from water and acetonitrile to give 42 mg (92%) of the title compound.

$^1$H NMR (300 MHz, $CDCl_3$) δ 7.95 (bt, 1H), 7.2-7.1 (m, 4H), 6.99 (m, 1H), 6.52 (t, 1H), 4.88 (s, 1H), 4.85-4.75 (m, 3H), 4.6-4.45 (m, 2H), 4.29 (broad, 1H), 4.09 (m, 1H), 3.89 (s, 3H), 3.69 (m, 1H), 2.64 (m, 1H), 2.38 (m, 1H), 1.85 (broad, 1H) $^{13}$C-NMR (100 MHz; $CDCl_3$): (carbonyl and/or amidine carbons) δ 172.1, 169.8, 151.9

APCI-MS: (M+1)=533/535 m/z

Preparation C

Preparation of Compound C

(i) (2-Monofluoroethyl) Methanesulfonate

To a magnetically stirred solution of 2-fluoroethanol (5.0 g, 78.0 mmol) in $CH_2Cl_2$ (90 mL) under nitrogen at 0° C. was added triethylamine (23.7 g, 234 mmol) and methanesulfonyl chloride (10.7 g, 93.7 mmol). The mixture was stirred at 0° C. for 1.5 h, diluted with $CH_2Cl_2$ (100 mL) and washed with 2N HCl (100 mL). The aqueous layer was extracted with $CH_2Cl_2$ (50 mL) and the combined organic extracts washed with brine (75 mL), dried ($Na_2SO_4$), filtered and concentrated in vacuo to afford the sub-title compound (9.7 g, 88%) as a yellow oil which was used without further purification.

$^1$H NMR (300 MHz, $CDCl_3$) δ 4.76 (t, J=4 Hz, 1H), 4.64 (t, J=4 Hz, 1H), 4.52 (t, J=4 Hz, 1), 4.43 (t, J=4 Hz, 1H), 3.09 (s, 3H).

(ii) 3-Chloro-5-monofluoroethoxybenzaldehyde

To a solution of 3-chloro-5-hydroxybenzaldehyde (8.2 g, 52.5 mmol; see Preparation A (ii) above) and potassium carbonate (9.4 g, 68.2 mmol) in DMF (10 mL) under nitrogen was added a solution of (2-monofluoroethyl)methanesulfonate (9.7 g, 68.2 mmol; see step (i) above) in DMF (120 mL) dropwise at room temperature. The mixture was heated to 100° C. for 5 h and then stirred overnight at room temperature. The reaction was cooled to 0° C., poured into ice-cold 2N HCl and extracted with EtOAc. The combined organic extracts were washed with brine, dried ($Na_2SO_4$), filtered and concentrated in vacuo. The brown oil was chromatographed on silica gel eluting with Hex:EtOAc (4:1) to afford the sub-title compound (7.6 g, 71%) as a yellow oil.

$^1$H NMR (300 MHz, $CDCl_3$) δ 9.92 (s, 1H), 7.48 (s, 1H), 7.32 (s, 1H), 7.21 (s, 1H), 4.87 (t, J=4 Hz, 1H), 4.71 (t, J=3 Hz, 1H) 4.33 (t, J=3 Hz, 1H), 4.24 (t, J=3 Hz, 1H).

(iii) Ph(3-Cl)(5-OCH₂CH₂F)—(R,S)CH(OTMS)CN

To a solution of 3-chloro-5-monofluoroethoxybenzaldehyde (7.6 g, 37.5 mmol; see step (ii) above) and zinc iodide (3.0 g, 9.38 mmol) in $CH_2Cl_2$ (310 mL) was added trimethylsilyl cyanide (7.4 g, 75.0 mmol) dropwise at 0° C. under nitrogen. The mixture was stirred at 0° C. for 3 h and at room temperature overnight. The reaction was diluted with $H_2O$ (300 mL), the organic layer was separated, dried ($Na_2SO_4$), filtered and concentrated in vacuo to afford the sub-title compound (10.6 g, 94%) as a brown oil that was used without further purification or characterisation.

(iv) Ph(3-Cl)(5-OCH₂OCH₂F)—(R,S)CH(OH)C(O)OH

Concentrated hydrochloric acid (100 mL) was added to Ph(3-Cl)(5-OCH₂CH₂F)—(R,S)CH(OTMS)CN (10.6 g, 5.8 mmol; see step (iii) above) and the solution stirred at 100° C. for 3 h. After cooling to room temperature, the reaction was further cooled to 0° C., basified slowly with 3N NaOH (~300 mL) and washed with $Et_2O$ (3×200 mL). The aqueous layer was acidified with 2N HCl (80 mL) and extracted with EtOAc (3×300 mL). The combined EtOAc extracts were dried ($Na_2SO_4$), filtered and concentrated in vacuo to afford the sub-title compound (8.6 g, 98%) as a pale yellow solid that was used without further purification.

$R_f$=0.28 (90:8:2 $CHCl_3$:MeOH:concentrated $NH_4OH$)

$^1$H NMR (300 MHz, $CD_3OD$) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(v) Ph(3-Cl)(5-OCH₂CH₂F)—(S)CH(OAc)C(O)OH (a) and Ph(3-Cl)(5-OCH₂CH₂F)—(R)CH(OH)C(O)OH (b)

A solution of Ph(3-Cl)(5-OCH₂CH₂F)—(R,S)CH(OR)C(O)OH (8.6 g, 34.5 mmol; see step (iv) above) and Lipase PS "Amano" (4.0 g) in vinyl acetate (250 mL) and MTBE (250 mL) was heated at 70° C. under nitrogen for 3 d. The reaction was cooled to room temperature and the enzyme removed by filtration through Celite®. The filter cake was washed with EtOAc and the filtrate concentrated in vacuo. Chromatography on silica gel eluting with $CHCl_3$:MeOH:$Et_3N$ (90:8:2) afforded the triethylamine salt of sub-title compound (a) as a yellow oil. In addition, the triethylamine salt of sub-title compound (b) (4.0 g) was obtained. The salt of sub-title compound (b) was dissolved in $H_2O$ (250 mL), acidified with 2N HCl and extracted with EtOAc (3×200 mL). The combined organic extracts were dried ($Na_2SO_4$), filtered and concentrated in vacuo to yield the sub-title compound (b) (2.8 g, 32%) as a yellow oil.

Data for Sub-Title Compound (b):

$R_f$=0.28 (90:8:2 $CHCl_3$:MeOH:concentrated $NH_4OH$)

$^1$H NMR (300 MHz, $CD_3OD$) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(vi) Compound C

To a solution of Ph(3-Cl)(5-OCH₂CH₂F)—(R)CH(OH)C(O)OH (818 mg, 3.29 mmol; see step (v) above) in DMF (30 mL) under nitrogen at 0° C. was added HAze-Pab(OMe).2HCl (1.43 g, 4.27 mmol, see international patent application WO 00/42059), PyBOP (1.89 g, 3.68 mmol), and DIPEA (1.06 g, 8.23 mmol). The reaction was stirred at 0° C. for 2 h and then at room temperature overnight. The mixture was concentrated in vacuo and the residue chromatographed two times on silica gel, eluting first with $CHCl_3$:EtOH (15:1) and second with EtOAc:EtOH (20:1) to afford the title compound (880 mg, 54%).

$R_f$=0.60 (10:1 $CHCl_3$:EtOH)

$^1$H NMR (300 MHz, $CD_3OD$, complex mixture of rotamers) δ 7.58-7.60 (d, J=8 Hz, 2H), 7.34 (d, J=7 Hz, 2H), 7.05-7.08 (m, 2H), 6.95-6.99 (m, 1H), 5.08-5.13 (m, 1H), 4.77-4.82 (m, 1H), 4.60-4.68 (m, 1H), 3.99-4.51 (m, 7H), 3.82 (s, 3H), 2.10-2.75 (m, 2H).

$^{13}$C-NMR (150 MHz; $CD_3OD$), (carbonyl and/or amidine carbons) a 173.3, 170.8, 152.5.

APCI-MS: (M+1)=493 m/z.

Examples 1 and 2

Preparation of Salts of Compound A

Example 1

General Method for Salt Preparation

The following generic method was employed to prepare salts of Compound A; 200 mg of Compound A (see Preparation A above) was dissolved in 5 mL of MeOH. To this solution was added a solution of the relevant acid (1.0 molar equivalent) dissolved in 5 mL of MeOH. After stirring for 10 minutes at room temperature, the solvent was removed by way of a rotary evaporator. The remaining solid material was re-dissolved in 8 mL of acetonitrile; H₂O (1:1). Freeze-drying afforded colorless amorphous material in each case.

Acids Employed:

(1S)-(+)-10-camphorsulfonic malic cyclohexylsulphamic phosphoric dimethylphosphoric p-toluenesulphonic L-lysine L-lysine hydrochloride saccharinic methanesulphonic hydrochloric Appropriate characterising data are shown in Table 1.

TABLE 1

| Salt | Mw acid | Mw salt | LRMS | Δ ppm (MeOD) H18, H19, H24 (see structure at end of Example 9 below) |
|---|---|---|---|---|
| (1S)-(+)-10-camphorsulfonate | 232.20 | 729.20 | 230.9 495.1 497.0 727.3 | 7.57, 7.68, 3.97 |
| maleate | 116.07 | 612.97 | 114.8 495.1 497.0 | 7.45, 7.64, 3.89 |
| cyclohexylsulphamate | 179.24 | 676.14 | 177.9 495.1 496.9 674.3 676.1 | 7.44, 7.64, 3.89 |
| phosphate | 97.99 | 594.89 | 495.1 497.0 593.1 | 7.37, 7.61, 3.84 |
| dimethylphosphate | 126.05 | 622.95 | 124.9 495.1 497.0 621.2 623.0 | 7.50, 7.66, 3.92 |
| p-toluenesulphonate | 172.20 | 669.10 | 170.9 495.1 497.0 | 7.54, 7.71, 3.95 |
| L-lysine | 146.19 | 643.09 | 145.0 495.1 497.0 | 7.36, 7.60, 3.83 |
| L-lysine hydrochloride | 182.65 | 679.55 | 495.1 497.0 531.1 (HCl) | 7.36, 7.60, 3.83 |
| saccharinate | 183.19 | 680.09 | 181.9 495.1 497.0 | 7.44, 7.64, 3.89 |
| methanesulphonate | 96.11 | 593.01 | 495.1 497.0 591.2 593.1 | 7.57, 7.68, 3.97 |
| hydrochloride | 36.46 | 533.36 | 495.1 496.9 531.1 532.5 535.2 | 7.55, 7.67, 3.95 |

All salts formed in this Example were amorphous.

Example 2

Further amorphous salts of Compound A were made using analogous techniques to those described in Example 1 above from the following acids:

hydrobromic acid (1:1 salt)

hydrochloric acid (1:1 salt)

sulphuric acid (1:0.5 salt)

1,2-ethanedisulfonic acid (1:0.5 salt)

1S-camphorsulfonic acid (1:1 salt)

(+/−)-camphorsulfonic acid (1:1 salt)

ethanesulfonic acid (1:1 salt)

nitric acid (1:1 salt)

toluenesulfonic acid (1:1 salt)

methanesulfonic acid (1:1 salt)

p-xylenesulfonic acid (1:1 salt)

2-mesitylenesulfonic acid (1.1 salt)

1,5-naphthalenesulfonic acid (1:0.5 salt)

naphthalenesulfonic acid (1:1 salt)

benzenesulfonic acid (1:1 salt)

saccharinic acid (1:1 salt)

maleic acid (1:1 salt)

phosphoric acid (1:1 salt)

D-glutamic acid (1:1 salt)

L-glutamic acid (1:1 salt)

D,L-glutamic acid (1:1 salt)

L-arginine (1:1 salt)

L-lysine (1:1 salt)

L-lysine hydrochloride (1:1 salt)

glycine (1:1 salt)

salicylic acid (1:1 salt)

tartaric acid (1:1 salt)

fumaric acid (1:1 salt)

citric acid (1:1 salt)

L-(−)-malic acid (1:1 salt)

D,L-malic acid (1.1 salt)

D-gluconic acid (1:1 salt)

Example 3

Preparation of Amorphous Compound A, Ethanesulfonic Acid Salt

Compound A (203 mg; see Preparation A above) was dissolved in ethanol (3 ml) and ethanesulfonic acid (1 eq., 95%, 35 μL) was added to the solution. The mixture was stirred for a few minutes, and then the solvent was evaporated. The resulting oil was slurried in iso-octane and evaporated to dryness until a solid material was obtained. Finally, the substance was re-slurried in iso-octane and the solvent evaporated again resulting in a white, dry, amorphous solid. The substance was vacuum dried at 40° C. overnight.

Examples 4 to 9

Preparation of Crystalline Compound A, Ethanesulfonic Acid Salt

Example 4

Crystallisation of Amorphous Material

Amorphous Compound A, ethanesulfonic acid salt (17.8 mg; see Example 3 above) was slurried in methyl iso-butyl ketone (600 µL). After 1 week, crystalline needles were observed, which were filtered off and air-dried.

Examples 5 TO 7

Reaction Crystallisations (Without Anti-Solvent)

Example 5

Compound A (277 mg; see Preparation A above) was dissolved in methyl isobutyl ketone (3.1 ml). Ethanesulfonic acid was added (1 eq., 95%, 48 µL). Precipitation of amorphous ethanesulfonate salt occurred immediately. More methyl iso-butyl ketone (6 mL) was added and the slurry was treated with ultrasound. Finally, a third portion of methyl iso-butyl ketone (3.6 mL) was added and then the slurry was left overnight with stirring (magnetic stirrer). The next day, the substance had transformed into crystalline needles. The slurry was filtered off, washed with methyl iso-butyl ketone (0.5 mL) and air dried.

Example 6

Compound A (236 mg; see Preparation A above) was dissolved at room temperature in methyl iso-butyl ketone (7 mL). Ethanesulfonic acid (1 eq., 41 µL) was mixed with 2 mL of methyl iso-butyl ketone in a vial. The solution of Compound A was seeded with crystalline Compound A, ethanesulfonic acid salt (see Examples 4 and 5 above). Then, 250 µL of the methyl iso-butyl ketone solution of ethanesulfonic acid was added in portions over 45 minutes. The solution was seeded again, and the temperature was increased to 30° C. Then, 500 µL of the methyl iso-butyl ketone solution was added over approximately 1 hour. The resulting slurry was left overnight before a final amount of the methyl iso-butyl ketone/acid solution was added over 20 minutes. The vial was rinsed with 1.5 mL of methyl iso-butyl ketone, which was added to the slurry. After a further 6 hours, the crystals were filtered off, washed with methyl iso-butyl ketone (2 mL) and dried under reduced pressure at 40° C. A total of 258 mg of crystalline salt was obtained which corresponds to a yield of approximately 87%.

Example 7

Compound A (2.36 g; see Preparation A above) was dissolved in methyl iso-butyl ketone (90 mL). Seed crystals (10 mg) of Compound A, ethanesulfonic acid salt (see Examples 4 to 6 above) were added to the solution, and then ethanesulfonic acid (40 µL) was added in two portions. Further seed crystals (12 mg) and two portions of ethanesulfonic acid (2×20 µL) were then added. The slurry was diluted with methyl iso-butyl ketone (15 mL) before the addition of ethanesulfonic acid was continued. A total amount of 330 µL ethanesulfonic acid was added, in portions, over 1 hour. A small amount of seed crystals was added and, finally, the slurry was left overnight with stirring. The next day, the crystals were filtered off, washed with methyl iso-butyl ketone (2×6 mL) and dried under reduced pressure at 40° C. After drying, a total of 2.57 g of white, crystalline product was obtained corresponding to a yield of 89%.

Examples 8 and 9

Reaction Crystallizations (with Anti-Solvent)

Example 8

Compound A (163 mg; see Preparation A above) was dissolved in iso-propanol (1.2 mL). The solution was heated to 35° C. Ethanesulfonic acid was added (28 µL). Then, ethyl acetate (4.8 mL) was added and the solution was seeded with crystalline Compound A, ethanesulphonic acid salt (see Examples 4 to 7 above). Crystallization started almost immediately. The slurry was left for about 80 minutes at 35° C. before being allowed to cool to ambient temperature (21° C.). Two hours later, the crystals were filtered off, washed three times with ethyl acetate (3×0.4 mL), and dried under reduced pressure at 40° C. A total of 170 mg of crystalline title product was obtained which corresponds to a yield of approximately 82%.

Example 9

Compound A (20.0 g; see Preparation A above) was dissolved in iso-propanol (146.6 ml) at 40° C. and ethanesulfonic acid (3.46 mL, 95%, 1 eq.) was added to the solution. To the resulting clear solution, seed crystals of Compound A, ethanesulfonic acid salt were added (50 mg; see Examples 4 to 8 above). Then, ethyl acetate (234 mL) was added over 10 minutes. The resulting slightly opaque solution was seeded once more (70 mg) and left for one hour at 40° C. with stirring to allow for crystallization to start. After this, a total of 352 mL of ethyl acetate was added at a constant rate over one hour. When all of the ethyl acetate had been added, the slurry was left for 1 hour, before being cooled to 21° C. over 2 hours. The crystallization was allowed to continue for 1 hour at 21° C. before the crystals were filtered off, washed twice with ethyl acetate (50 ml+60 mL) and finally, dried under reduced pressure at 40° C. overnight. A total of 21.6 g of a white, crystalline salt was obtained, corresponding to a yield of approximately 90%.

Compound A, ethanesulfonic acid salt was characterised by NMR as follows: 23 mg of the salt was dissolved in deuterated methanol (0.7 ml) troscopy.

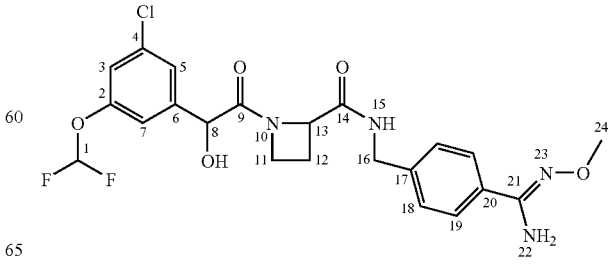

A combination of 1D ($^1$H, $^{13}$C and selective NOE) and 2D (gCOSY, gHSQC and gHMBC) NMR experiments were used. All data were in good agreement with the theoretical structure of the salt, shown below. The molecule exists in two conformations in methanol. Based on the integral of the peak assigned to H5 (dominant conformer) and peak assigned to H5 (other conformer), the ratio between the two conformers was found to be 70:30. H22 could not be observed as these protons were in fast exchange with the solvent CD$_3$OD.

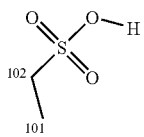

Both the proton and the carbon resonance corresponding to position 1 are split due to the spin-coupling with the two fluorine nuclei in that position. The coupling constants are $^2J_{HF}$=73 Hz and $^1J_{CF}$=263 Hz.

$^1$H and $^{13}$C NMR chemical shift assignment and proton-proton correlations are shown in Table 2.

TABLE 2

| Atom No. | Type | $^{13}$C shift/ ppm$^a$ | $^1$H shift/ppm$^b$ and multiplicity$^c$ | $J_{HH}$/Hz |
|---|---|---|---|---|
| 1 | CH | 117.5$^e$ | 6.90 (t) | 73 ($^2J_{HF}$) |
| 1' |  | 117.5$^e$ | 6.88 (t) |  |
| 2 | C | 153.5 |  |  |
| 2' |  | 153.5 |  |  |
| 3 | CH | 120.0 | 7.15 (s) |  |
| 3' |  | 119.7 | 7.13 (s) |  |
| 4 | C | 136.2 |  |  |
| 4' |  | 135.9 |  |  |
| 5 | CH | 125.0 | 7.36 (s) |  |
| 5' |  | 124.9 | 7.31 (s) |  |
| 6 | C | 144.5 |  |  |
| 6' |  | 145.3 |  |  |
| 7 | CH | 117.3 | 7.20 (s) |  |
| 7' |  | 117.2 | 7.15 (s) |  |
| 8 | CH | 72.0 | 5.20 (s) |  |
| 8' |  | 74.0 | 5.12 (s) |  |
| 9 | CO | 173.1 |  |  |
| 9' |  | 173.8 |  |  |
| 11 | CH$_2$ | 51.6 | a: 4.38 (m) |  |
|  |  |  | b: 4.21 (m) |  |
| 11' |  | 49.0 | a: 4.06 (m) |  |
|  |  |  | b: 3.99 (m) |  |
| 12 | CH$_2$ | 21.7 | a: 2.55 (m) |  |
|  |  |  | b: 2.29 (m) |  |
| 12' |  | 23.2 | a: 2.70 (m) |  |
|  |  |  | b: 2.15 (m) |  |
| 13 | CH | 63.1 | 4.80 (m) |  |
| 13' |  | 66.2 | 5.22 (m) |  |
| 14 | CO | 172.9 |  |  |
| 14' |  | 173.6 |  |  |
| 15 | NH |  | 8.76 (t, br) | 5.2 |
| 15' |  |  | 8.79 (t, br) | 5.2 |
| 16 | CH$_2$ | 43.5 | 4.59 (AB-pattern) | 15.9 |
|  |  |  | 4.46 (AB-pattern) | 15.9 |
| 16' |  | 43.6 | 4.53 (AB-pattern) | 15.9 |
|  |  |  | 4.49 (AB-pattern) | 15.9 |
| 17 | C | 146.9 |  |  |
| 17' |  | 147.0 |  |  |
| 18 | CH | 129.1 | 7.56 (d) | 7.8 |
| 18' |  | 129.1 | 7.57 (d) | 7.8 |
| 19 | CH | 129.2 | 7.67 (d) | 7.8 |
| 19' |  | 129.4 | 7.70 (d) | 7.8 |
| 20 | C | 124.9 | — |  |
| 20' |  | 124.9 |  |  |
| 21 | C | 162.4 |  |  |
| 21' |  | 162.3 |  |  |
| 22 | NH$_2$ |  | Not observed |  |
| 24 | CH$_3$ | 64.8 | 3.96 (s) |  |
| 101 | CH3 |  | 1.28 (t) | 7.4 |
| 102 | CH2 |  | 2.77 (m) | 7.4 |

$^a$Relative to the solvent resonance at 49.0 ppm.
$^b$Relative to the solvent resonance at 3.30 ppm.
$^c$s = singlet, t = triplet, m = multiplet, br = broad, d = doublet
$^d$Obtained in the gCOSY experiment.
$^e$The resonance is a triplet due to coupling with the two fluorine nuclei. $^1J_{CF}$ = 263 Hz.

HRMS calculated for $C_{24}H_{29}ClF_2N_4O_8S$ (M-H)$^-$ 605.1284, found 605.1296.

Crystals of Compound A, ethanesulfonic acid salt (obtained by way of one or more of Examples 4 to 9 above) were analyzed by XRPD and the results are tabulated below (Table 3) and are shown in FIG. 1.

TABLE 3

| d value (Å) | Intensity (%) | Intensity |
|---|---|---|
| 16.5 | 10 | m |
| 12.2 | 74 | vs |
| 11.0 | 4 | w |
| 9.0 | 33 | s |
| 8.3 | 3 | vw |
| 7.6 | 6 | w |
| 6.4 | 4 | w |
| 6.2 | 12 | m |
| 6.0 | 7 | m |
| 5.9 | 10 | m |
| 5.5 | 15 | m |
| 5.4 | 100 | vs |
| 5.1 | 7 | m |
| 4.66 | 29 | s |
| 4.60 | 36 | s |
| 4.31 | 57 | s |
| 4.25 | 18 | m |
| 4.19 | 20 | m |
| 4.13 | 12 | m |
| 4.00 | 12 | m |
| 3.87 | 13 | m |
| 3.83 | 6 | w |
| 3.76 | 7 | m |
| 3.72 | 6 | w |
| 3.57 | 9 | m |
| 3.51 | 7 | m |
| 3.47 | 5 | w |
| 3.39 | 3 | vw |
| 3.31 | 11 | m |
| 3.26 | 10 | m |
| 3.21 | 8 | m |
| 3.16 | 4 | w |
| 3.03 | 8 | m |
| 2.78 | 4 | w |
| 2.74 | 5 | w |
| 2.67 | 3 | vw |
| 2.56 | 5 | w |
| 2.50 | 5 | w |
| 2.46 | 7 | m |
| 2.34 | 4 | w |
| 2.21 | 5 | w |
| 2.00 | 3 | vw |
| 1.98 | 3 | vw |

DSC showed an endotherm with an extrapolated melting onset temperature of ca. 131° C. TGA showed a decrease in mass of ca. 0.2% (w/w) around the melting point. DSC analysis repeated with a sample of lower solvent content showed a melting onset temperature of ca. 144° C.

Example 10

Preparation of Amorphous Compound A, Benzenesulfonic Acid Salt

Compound A (199 mg; see Preparation A above) was dissolved in ethanol (2 μL). Benzenesulfonic acid (1 eq. 90%, 70 mg) was dissolved in ethanol (1 μL) in a vial. The ethanol solution of the acid was added to the solution of Compound A and the vial was rinsed with 1 at ethanol, which was then added to the mixture. The mixture was stirred for a few minutes, and then the ethanol was evaporated until an oil was formed. Ethyl acetate (3 mL) was added and the solvent was evaporated again to dryness. An amorphous solid was formed.

Examples 11 TO 13

Preparation of Crystalline Compound A, Benzenesulfonic Acid Salt

Example 11

Crystallisation of Amorphous Material

Amorphous Compound A benzenesulfonic acid salt (20.7 mg; see Example 10 above) was slurried in ethyl acetate (600 μL). After 5 days, crystalline needles were observed in the slurry.

Examples 12 AND 13

Reaction Crystallisations

Example 12

Compound A (128 mg; see Preparation A above) was dissolved in ethyl acetate (3 mL). The solution was seeded with the slurry from Example 11 above. Then, benzenesulfonic acid was added (1 eq., 90%, 45 mg). Precipitation of benzenesulphonic acid salt occurred immediately. iso-Propanol was added to the slurry (0.8 μL) and the mixture was seeded again, Two days later, the substance had transformed into crystalline needles. The slurry was filtered off, washed with ethyl acetate (3×0.2 μL) and dried for a short time under vacuum at 40° C. A total of approximately 140 mg of white solid was obtained.

Example 13

Compound A (246 mg; see Preparation A above) was dissolved in iso-propanol (1.52 ml). Benzenesulfonic acid was added (88 mg, 90%). To the clear solution, ethyl acetate was added (3 mL), and then the mixture was seeded to initiate crystallisation. After 1 hour, more ethyl acetate was added (2.77 mL). Finally, the slurry was allowed to crystallise overnight before the crystals were filtered off, washed with ethyl acetate (3×0.3 mL) and dried at 40° C. under vacuum. A total of 279 mg salt was obtained which corresponds to a yield of approximately 86%.

Compound A, benzenesulfonic acid salt was characterised by NMR as follows: 20 mg of the salt was dissolved in deuterated methanol (0.7 mL). A combination of 1D ($^1$H, $^{13}$C and selective NOE) and 2D (gCOSY, gHSQC and gHMBC) NMR experiments were used. All data were in good agreement with the theoretical structure of the salt, shown below. The molecule exists in two conformations in methanol. Based on the integral of the peak assigned to H12 (dominant conformer) and peak assigned to H12' (other conformer), the ratio between the two conformers was found to be 70:30. H22 could not be observed as these protons were in fast exchange with the solvent CD$_3$OD.

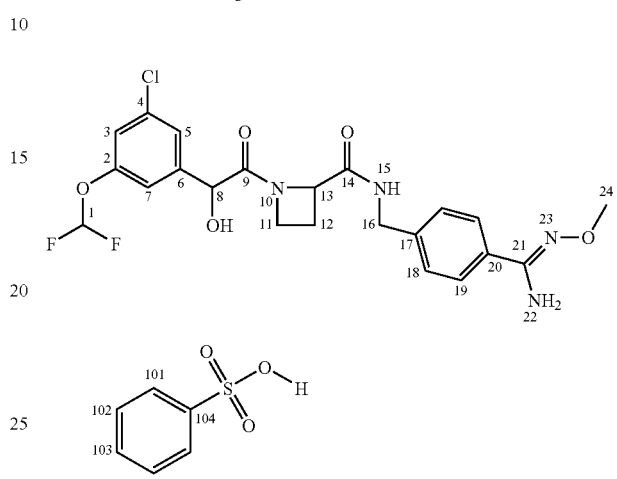

Both the proton and the carbon resonance corresponding to position 1 are split due to the spin-coupling with the two fluorine nuclei in that position. The coupling constants are $^2J_{HF}$=74 Hz and $^1J_{CF}$=260 Hz.

$^1$H and $^{13}$C NMR chemical shift assignment and proton-proton correlations are shown in Table 4.

TABLE 4

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CH | 117.5$^e$ | 6.89 (t) | 74 ($^2J_{HF}$) |
| 1' | | 117.5$^e$ | 6.87 (t) | |
| 2 | C | 153.5 | | |
| 2' | | 153.5 | | |
| 3 | CH | 120.1 | 7.15 (s) | |
| 3' | | 119.7 | 7.12 (s) | |
| 4 | C | 136.2 | | |
| 4' | | 135.9 | | |
| 5 | CH | 125.1 | 7.35 (s) | |
| 5' | | 124.9 | 7.31 (s) | |
| 6 | C | 144.5 | | |
| 6' | | 145.3 | | |
| 7 | CH | 117.3 | 7.20 (s) | |
| 7' | | 117.2 | 7.14 (s) | |
| 8 | CH | 72.8 | 5.20 (s) | |
| 8' | | 74.0 | 5.12 (s) | |
| 9 | CO | 173.1 | | |
| 9' | | 173.8 | | |
| 11 | CH$_2$ | 51.6 | a: 4.37 (m) | |
| | | | b: 4.20 (m) | |
| 11' | | 49.0 | a: 4.05 (m) | |
| | | | b: 3.98 (m) | |
| 12 | CH$_2$ | 21.7 | a: 2.53 (m) | |
| | | | b: 2.28 (m) | |
| 12' | | 23.2 | a: 2.69 (m) | |
| | | | b: 2.14 (m) | |
| 13 | CH | 63.1 | 4.79 (m) | |
| 13' | | 66.2 | 5.22 (m) | |
| 14 | CO | 172.9 | | |
| 14' | | 173.6 | | |
| 15 | NH | | 8.75 (t, br) | 5.3 |
| 15' | | | 8.78 (t, br) | 5.3 |

TABLE 4-continued

| Atom No. | Type | $^{13}$C shift/ppm$^a$ | $^1$H shift/ppm$^b$ and multiplicity$^c$ | $J_{HH}$/Hz |
|---|---|---|---|---|
| 16 | CH$_2$ | 43.5 | 4.59 (AB-pattern) | 16.0 and 5.2 |
|  |  |  | 4.44 (AB-pattern) | 16.0 and 4.8 |
| 16' |  | 43.6 | 4.51 (AB-pattern) | 16.0 |
|  |  |  | 4.46 (AB-pattern) | 16.0 |
| 17 | C | 146.9 |  |  |
| 17' |  | 147.0 |  |  |
| 18 | CH | 129.2 | 7.54 (d) | 8.3 |
| 18' |  | 129.2 | 7.56 (d) | 8.3 |
| 19 | CH | 129.3 | 7.66 (d) | 8.3 |
| 19' |  | 129.4 | 7.69 (d) | 8.3 |
| 20 | C | 124.9 | — |  |
| 20' |  | 124.9 |  |  |
| 21 | C | 162.4 |  |  |
| 21' |  | 162.4 |  |  |
| 22 | NH$_2$ |  | Not observed |  |
| 24 | CH$_3$ | 64.8 | 3.95 (s) |  |
| 101 | CH | 126.9 | 7.81 (m) |  |
| 102 | CH | 129.1 | 7.41 (m) |  |
| 103 | CH | 131.2 | 7.42 (m) |  |
| 104 | C | 146.4 |  |  |

$^a$Relative to the solvent resonance at 49.0 ppm.
$^b$Relative to the solvent resonance at 3.30 ppm.
$^c$s = singlet, t = triplet, m = multiplet, br = broad, d = doublet.
$^d$Obtained in the gCOSY experiment.
$^e$The resonance is a triplet due to coupling with the two fluorine nuclei. $^1J_{CF}$ = 260 Hz.
$^f$connectivity difficult to determine due to overlap between resonance 102 and 103

Figure 2:
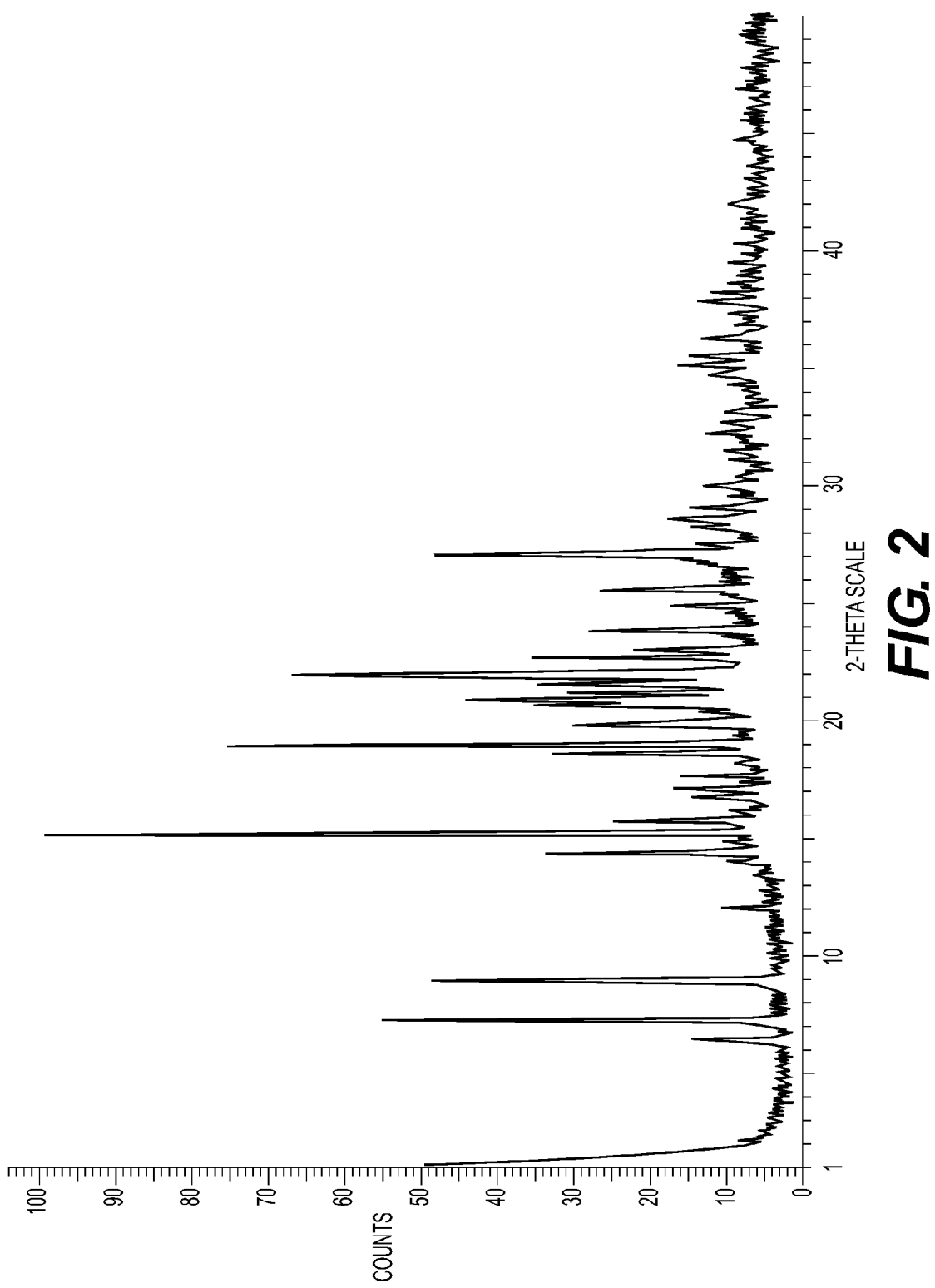
FIG. 2 shows an X-ray powder diffractogram for crystalline Compound A, benzenesulfonic acid salt.

HRMS calculated for $C_{28}H_{29}ClF_2N_4O_8S$ (M-H)$^-$ 653.1284, found 653.1312. Crystals of Compound A, benzenesulfonic acid salt (obtained by way of one or more of Examples 11 to 13 above) were analyzed by XRPD and the results are tabulated below (Table 5) and are shown in FIG. 2.

TABLE 5

| d value (Å) | Intensity (%) | Intensity |
|---|---|---|
| 14.2 | 12 | m |
| 12.6 | 55 | s |
| 10.2 | 49 | s |
| 7.5 | 8 | m |
| 6.4 | 5 | w |
| 6.3 | 30 | s |
| 6.1 | 5 | w |
| 5.9 | 100 | vs |
| 5.7 | 20 | m |
| 5.4 | 9 | m |
| 5.3 | 11 | m |
| 5.1 | 10 | m |
| 4.96 | 3 | vw |
| 4.83 | 27 | s |
| 4.73 | 72 | vs |
| 4.54 | 23 | s |
| 4.50 | 10 | m |
| 4.35 | 28 | s |
| 4.30 | 38 | s |
| 4.24 | 24 | s |
| 4.17 | 28 | s |
| 4.09 | 60 | vs |
| 4.08 | 61 | vs |
| 3.96 | 29 | s |
| 3.91 | 15 | m |
| 3.77 | 22 | s |
| 3.62 | 11 | m |
| 3.52 | 20 | m |
| 3.31 | 44 | s |
| 3.19 | 8 | m |
| 3.15 | 11 | m |
| 3.09 | 8 | m |
| 3.00 | 7 | m |
| 2.89 | 3 | vw |
| 2.86 | 4 | w |
| 2.79 | 7 | m |
| 2.76 | 6 | w |
| 2.72 | 5 | w |
| 2.59 | 6 | w |
| 2.56 | 9 | m |
| 2.54 | 9 | m |
| 2.49 | 7 | m |
| 2.38 | 8 | m |
| 2.16 | 4 | w |
| 2.03 | 3 | vw |

DSC showed an endotherm with an extrapolated melting onset temperature of ca. 152° C. TGA showed a decrease in mass of ca. 0.1% (w/w) around the melting point.

Example 14

Preparation of Amorphous Compound A, n-propanesulfonic Acid Salt

Compound A (186 mg; see Preparation A above) was dissolved in iso-propanol (1.39 mL) and n-propanesulfonic acid (1 eq. 95%, 39 µL) was added. Ethyl acetate (5.6 µL) was added and the solvent was evaporated until a dry, amorphous solid was formed.

Examples 15 AND 16

Preparation of Crystalline Compound A, n-propanesulfonic Acid Salt

Example 15

Crystallisation of Amorphous Material

Amorphous Compound A, n-propanesulfonic acid salt (20 mg; see Example 14 above) was dissolved in iso-propanol (60 µL) and iso-propyl acetate (180 µL) was added. After three days crystalline needles were observed.

Example 16

Reaction Crystallisation

Compound A (229 mg; see Preparation A above) was dissolved in iso-propanol (1.43 mL). n-Propanesulfonic acid was added (1 eq., 95%, 48 µL). Ethyl acetate was added (2 By), and then the solution was seeded with crystalline salt from Example 15 above. Further ethyl acetate was added (5 mL) and the slurry was left overnight to crystallize. The crystals were filtered off, washed with ethyl acetate (3×0.3 mL) and dried under vacuum at 40° C.

Compound A, n-propanesulfonic acid salt was characterised by NMR as follows: 13 mg of the salt was dissolved in deuterated methanol (0.7 mL) troscopy. A combination of 1D ($^1$H, $^{13}$C) and 2D (gCOSY) NMR experiments were used. All data were in good agreement with the theoretical structure of the salt, shown below. The molecule exists in two conformations in methanol. Based on the integral of the peak assigned to H12 (dominant conformer) and peak assigned to H12' (other conformer), the ratio between the two conformers was found to be 65:35. H22 could not be observed as these protons were in fast exchange with the solvent CD$_3$OD.

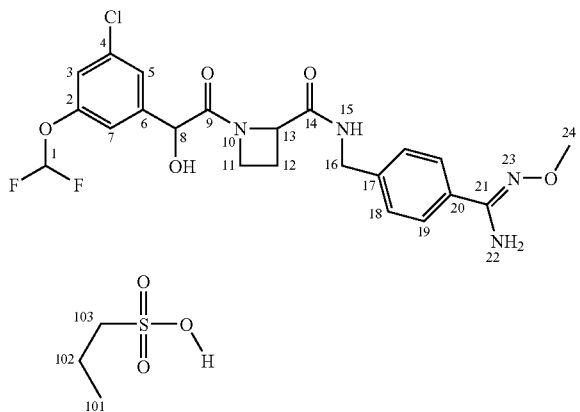

Both the proton and the carbon resonance corresponding to position 1 are split due to the spin-coupling with the two fluorine nuclei in that position. The coupling constants are $^2J_{HF}$=74 Hz and $^1J_{CF}$=260 Hz.

$^1$H and $^{13}$C NMR chemical shift assignment and proton-proton correlations are shown in Table 6.

TABLE 6

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CH | 117.5$^e$ | 6.89 (t) | 74 ($^2J_{HF}$) |
| 1' |  | 117.5$^e$ | 6.88 (t) |  |
| 2 | C | 153.5 |  |  |
| 2' |  | 153.5 |  |  |
| 3 | CH | 120.0 | 7.16 (s) |  |
| 3' |  | 119.7 | 7.13 (s) |  |
| 4 | C | 136.2 |  |  |
| 4' |  | 135.9 |  |  |
| 5 | CH | 125.1 | 7.36 (s) |  |
| 5' |  | 124.9 | 7.31 (s) |  |
| 6 | C | 144.5 |  |  |
| 6' |  | 145.3 |  |  |
| 7 | CH | 117.3 | 7.20 (s) |  |
| 7' |  | 117.2 | 7.16 (s) |  |
| 8 | CH | 72.9 | 5.20 (s) |  |
| 8' |  | 74.1 | 5.12 (s) |  |
| 9 | CO | 173.1 |  |  |
| 9' |  | 173.8 |  |  |
| 11 | CH$_2$ | 51.6 | a: 4.37 (m) |  |
|  |  |  | b: 4.20 (m) |  |
| 11' |  | 49.0 | a: 4.06 (m) |  |
|  |  |  | b: 3.98 (m) |  |
| 12 | CH$_2$ | 21.7 | a: 2.53 (m) |  |
|  |  |  | b: 2.29 (m) |  |
| 12' |  | 23.2 | a: 2.69 (m) |  |
|  |  |  | b: 2.15 (m) |  |
| 13 | CH | 63.1 | 4.80 (m) |  |
| 13' |  | 66.2 | 5.22 (m) |  |
| 14 | CO | 172.9 |  |  |
| 14' |  | 173.8 |  |  |
| 15 | NH |  | 8.75 (t, br) | 5.5 |
| 15' |  |  | 8.79 (t, br) | 5.5 |
| 16 | CH$_2$ | 43.5 | 4.59 (AB-pattern) | 16.0 and 6.6 |
|  |  |  | 4.45 (AB-pattern) | 16.0 and 5.3 |
| 16' |  | 43.6 | 4.51 |  |
|  |  |  | 4.50 |  |
| 17 | C | 146.9 |  |  |
| 17' |  | 147.0 |  |  |
| 18 | CH | 129.1 | 7.54 (d) | 8.5 |
| 18' |  | 129.2 | 7.57 (d) | 8.5 |
| 19 | CH | 129.2 | 7.67 (d) | 8.5 |
| 19' |  | 129.4 | 7.69 (d) | 8.5 |
| 20 | C | 124.9 | — |  |
| 20' |  | 124.9 |  |  |
| 21 | C | 162.4 |  |  |
| 21' |  | 162.4 |  |  |
| 22 | NH$_2$ |  | Not observed |  |
| 24 | CH$_3$ | 64.7 | 3.96 (s) |  |
| 101 | CH | 13.7 | 1.0 (t) |  |
| 102 | CH | 19.6 | 1.78 (m) |  |
| 103 | CH | 54.6 | 2.75 (m) |  |

$^a$Relative to the solvent resonance at 49.0 ppm.
$^b$Relative to the solvent resonance at 3.30 ppm.
$^c$s = singlet, t = triplet, m = multiplet, br = broad, d = doublet.
$^d$Obtained in the gCOSY experiment.
$^e$The resonance is a triplet due to coupling with the two fluorine nuclei. $^1J_{CF}$ = 260 Hz.

HRMS calculated for $C_{25}H_{31}ClF_2N_4O_8S$ (M-H)$^-$ 619.1441, found 619.1436.

Figure 3:
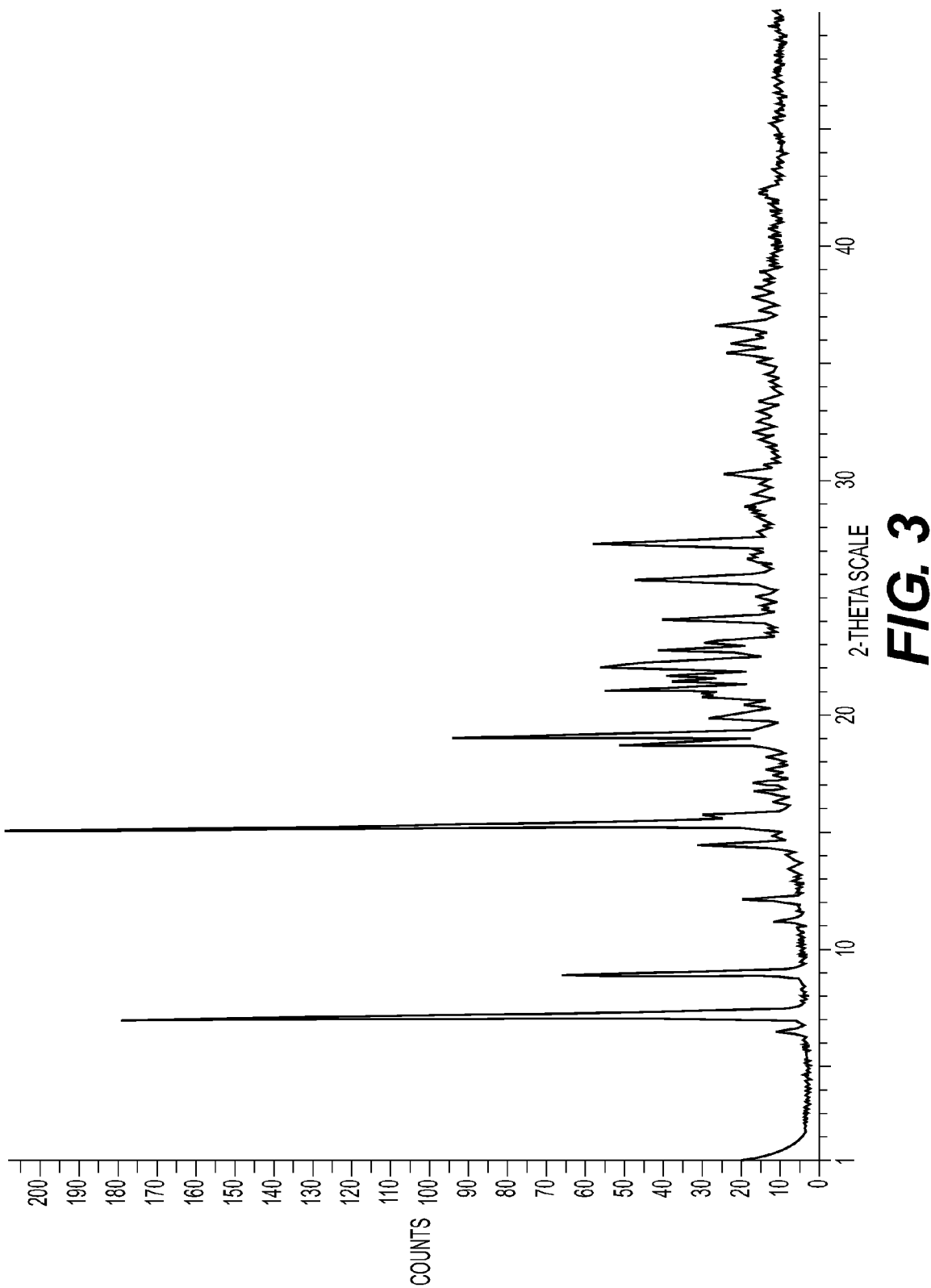
FIG. 3 shows an X-ray powder diffractogram for crystalline Compound A, n-propanesulfonic acid salt.

Crystals of Compound A, n-propanesulfonic acid salt (obtained by way of one or more of Examples 15 and 16 above) were analyzed by XRPD and the results are tabulated below (Table 7) and are shown in FIG. 3,

TABLE 7

| d value (Å) | Intensity (%) | Intensity |
|---|---|---|
| 14.0 | 4 | w |
| 12.4 | 87 | vs |
| 10.0 | 30 | s |
| 8.0 | 3 | vw |
| 7.5 | 7 | m |
| 7.0 | 0.6 | vw |
| 6.7 | 1 | vw |
| 6.4 | 1 | vw |
| 6.2 | 12 | m |
| 6.1 | 3 | vw |
| 5.8 | 100 | vs |
| 5.7 | 11 | m |
| 5.5 | 3 | vw |
| 5.4 | 5 | w |
| 5.3 | 5 | w |
| 5.2 | 2 | vw |
| 5.1 | 3 | vw |
| 4.94 | 3 | vw |
| 4.78 | 21 | s |
| 4.68 | 42 | s |
| 4.51 | 10 | m |
| 4.49 | 7 | m |
| 4.40 | 5 | w |
| 4.32 | 10 | m |
| 4.29 | 10 | m |
| 4.25 | 22 | s |
| 4.19 | 14 | m |
| 4.14 | 15 | m |
| 4.07 | 23 | s |
| 4.04 | 20 | m |
| 3.94 | 16 | m |
| 3.88 | 10 | m |
| 3.73 | 15 | m |
| 3.65 | 2 | vw |
| 3.59 | 3 | vw |
| 3.48 | 18 | m |
| 3.28 | 23 | m |
| 3.12 | 4 | w |
| 3.06 | 3 | vw |
| 2.97 | 6 | w |
| 2.84 | 2 | vw |
| 2.81 | 3 | vw |
| 2.76 | 2 | vw |
| 2.73 | 3 | vw |
| 2.70 | 2 | vw |
| 2.57 | 2 | vw |
| 2.54 | 6 | w |
| 2.51 | 6 | w |
| 2.46 | 8 | m |

TABLE 7-continued

| d value (Å) | Intensity (%) | Intensity |
|---|---|---|
| 2.42 | 2 | vw |
| 2.39 | 3 | vw |
| 2.36 | 3 | vw |
| 2.32 | 2 | vw |
| 2.14 | 3 | vw |
| 2.01 | 2 | vw |

DSC showed an endotherm with an extrapolated melting onset temperature of ca. 135° C. TGA showed no decrease in mass around the melting point.

Example 17

Example 17-A

Preparation of Amorphous Compound A n-butane Sulfonic Acid Salt

Amorphous Compound A (277 mg) was dissolved in IPA (1.77 ml) and butane sulfonic acid (approx. 1 eq 70 μL) was added. Ethyl acetate (6 ml) was added and the solvent was evaporated until dry, amorphous solid was formed.

Example 17-B

Preparation of Crystalline Compound a Butane Sulfonic Acid Salt

Amorphous Compound A butane sulfonic acid salt (71.5 mg; see preparation above) was slurried in ethyl acetate (500 μl) over night. The crystals were filtered off and were air-dried.

Compound A, butanesulfonic acid salt was charaterised by NMR as follows: 21.6 mg of the salt was dissolved in deuterated dimethylsulfoxide (0.7 ml) and was investigated with $^1$H and $^{13}$C NMR spectroscopy.

The spectra are very similar to other salts of the same compound and in good agreement with the structure shown below. Most resonances in the spectra are present as sets of two peaks due to the slow rotation around the C9-N10 bond, which results in two atropisomers that simultaneously exist in the solution. This is shown for other salts of the same compound.

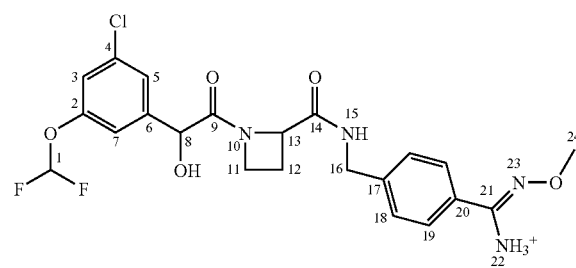

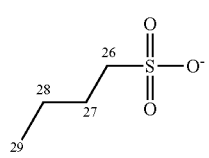

The two fluorine nuclei in position 1 give rise to split resonances for the proton and the carbon in that position. The coupling constants are $^2J_{HF}$=73 Hz and $^1J_{CF}$=258 Hz.

Chemical shifts for protons and carbons are presented in Table 1. Protons in position 22 and 24 are not detected due to chemical exchange. There is a very broad hump between 8 and 9 ppm in the proton spectrum corresponding to these protons.

TABLE 8

$^1$H and $^{13}$C NMR chemical shift assignment of Compound A n-butanesulfonate salt in deuterated dimethylsulfoxide at 25° C.

| Atom No. | Type | $^{13}$C shift/ ppm[a] | $^1$H shift/ppm[b] and multiplicity[c] | $J_{HH}$/Hz |
|---|---|---|---|---|
| 1 | CHF$_2$ | 116.3[d] | 7.29 (t) | 73 ($^2J_{HF}$) |
| 1' |  | 116.3[d] | 7.28 (t) | 73 ($^2J_{HF}$) |
| 2 | C | 151.5 | na | na |
| 2' |  | 151.3 | na | na |
| 3 | CH | 118.0 | 7.25 (t)[e] | nd |
| 3' |  | 117.6 | 7.21 (t)[e] | nd |
| 4 | C | 133.8 | na | na |
| 4' |  | 133.4 | na | na |
| 5 | CH | 123.8 | 7.34 (t)[e] | nd |
| 5' |  | 123.6 | 7.25 (t)[e] | nd |
| 6 | C | 144.5 | na | na |
| 6' |  | 145.2 | na | na |
| 7 | CH | 116.3 | 7.19 (t)[e] | nd |
| 7' |  | 116.1 | 7.12 (t)[e] | nd |
| 8 | CH | 70.9 | 5.13 (s) | na |
| 8' |  | 71.2 | 4.99 (s) | na |
| 9 | CO | 170.6 | na | na |
| 9' |  | 171.1 | na | na |
| 11 | CH$_2$ | 50.0 | a: 4.24 (m) b: 4.12 (m) | nd |
| 11' |  | 46.9 | 3.85 (m) | nd |
| 12 | CH$_2$ | 20.5 | a: 2.41 (m) b: 2.10 (m) | nd |
| 12' |  | 21.7 | a: 2.60 (m) b: 2.02 (m) | nd |
| 13 | CH | 61.2 | 4.65 (dd) | 5.6 and 8.9 |
| 13' |  | 63.9 | 5.12 (m) | nd |
| 14 | CO | 170.2 | na | na |
| 14' |  | 171.0 | na | na |
| 16 | CH$_2$ | 41.8 | 4.38 (m) | nd |
| 16' |  | 42.0 | 4.38 (m) | nd |
| 17 | C | 144.7 | na | na |
| 18 | CH | 127.5 | 7.44 (d) | 8.2 |
|  |  | 127.6 | 7.44 | nd |
| 19 | CH | 127.8 | 7.66 (d) | 8.2 |
| 20 | C | 125.1 | na | na |
| 21 | C | 157.9 | na | na |
| 24 | CH$_3$ | 63.3 | 3.83 (s) | na |
| 24' |  | 63.3 | 3.82 (s) | na |
| 26 | CH$_2$ | 51.4 | 2.41 (m) | nd |
| 27 | CH$_2$ | 27.3 | 1.52 (m) | nd |
| 28 | CH$_2$ | 21.7 | 1.30 (m) | nd |
| 29 | CH$_3$ | 14.0 | 0.83 (t) | 7.3 |

[a]Relative to the solvent resonance at 49.0 ppm.
[b]Relative to the solvent resonance at 3.30 ppm.
[c]s = singlet, d = doublet, dd = doublet of doublets, t = triplet, m = multiplet.
[d]The resonance is a triplet due to coupling with the two fluorine nuclei F1. $^1J_{CF}$ = 258 Hz.
[e]The $^4J_{HH}$ coupling with the meta-protons is not fully resolved.
na = not applicable,
nd = not determined HRMS calculated for $C_{26}H_{32}ClF_2N_4O_8S$ (M-H)$^-$ 633.1597, found 633.1600

Figure 4:
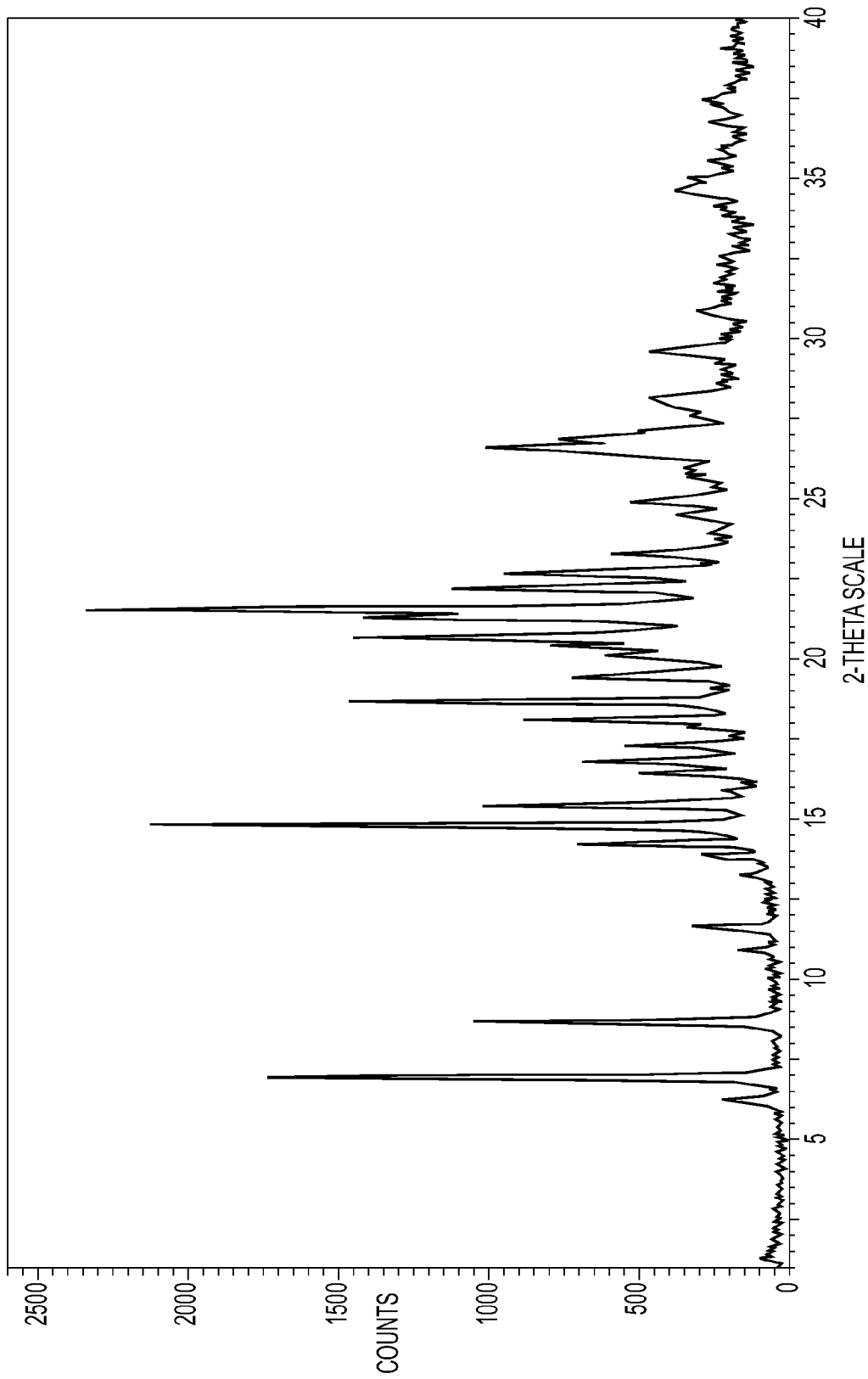
FIG. 4 shows an X-ray powder diffractogram for crystalline Compound A, n-butanesulfonic acid salt.

Crystals of Compound A n-butanesulfonic acid salt (obtained as described above in Example 17-B) were analyzed by XRPD and the results are tabulated below (Table 9) and are shown in FIG. 4.

TABLE 9

| d-value (Å) | Intensity (%) | Intensity |
|---|---|---|
| 14.3 | 8 | m |
| 12.8 | 81 | vs |
| 10.3 | 44 | s |
| 8.2 | 4 | w |
| 7.7 | 13 | m |
| 6.7 | 2 | vw |
| 6.4 | 8 | m |
| 6.2 | 18 | m |
| 6.0 | 100 | vs |
| 5.8 | 29 | s |
| 5.6 | 4 | w |
| 5.4 | 11 | m |
| 5.3 | 16 | m |
| 5.1 | 15 | m |
| 4.98 | 6.5 | w |
| 4.91 | 34 | s |
| 4.76 | 56 | s |
| 4.57 | 20 | m |
| 4.42 | 13 | m |
| 4.36 | 19 | m |
| 4.30 | 45 | s |
| 4.18 | 42 | s |
| 4.13 | 88 | vs |
| 4.01 | 34 | s |
| 3.92 | 28 | s |
| 3.82 | 18 | m |
| 3.64 | 6.6 | w |
| 3.58 | 16 | m |
| 3.47 | 5 | w |
| 3.44 | 6 | w |
| 3.38 | 12 | m |
| 3.35 | 32 | s |
| 3.32 | 22 | s |
| 3.29 | 12 | m |
| 3.20 | 8 | m |
| 3.17 | 9 | m |
| 3.02 | 12 | m |
| 2.90 | 6 | w |
| 2.81 | 3.9 | vw |
| 2.75 | 3 | vw |
| 2.64 | 3.5 | vw |
| 2.59 | 10 | m |
| 2.57 | 8 | m |
| 2.50 | 4 | w |
| 2.45 | 5 | w |
| 2.40 | 6 | w |
| 2.31 | 3 | vw |

DSC showed an endotherm with an extrapolated melting onset temperature of ca 118° C. and TGA showed an approximate 0.04% weight loss between 25 and 150° C.

Example 18

Preparation of Salts of Compound B

Example 18-A

General Method for Salt Preparation

The following generic method was employed to prepare salts of Compound B: 200 mg of compound B (see Preparation B above) was dissolved in 5 mL of MIBK (methyl isobutyl ketone). To this solution was added a solution of the relevant acid (1.0 or 0.5 molar equivalent, as indicated in Table 10) dissolved in 1.0 mL of MIBK. After stirring for 10 minutes at room temperature, the solvent was removed by way of a rotary evaporator. The remaining solid material was re-dissolved in about 8 mL of acetonitrile:$H_2O$ (1:1). Freeze-drying afforded colorless amorphous material in each case.

Acid Employed:

Esylate (ethanesulfonic acid)

Besylate (benzene sulfonic acid)

Cyclohexylsulphamate

Sulphate

Bromide p-Toluenesulphonate

2-Naphthalenesulfonate

Hemisulfate

Methanesulphonate

Nitrate

Hydrochloride

Appropriate characterising data are shown in Table 10

TABLE 10

| Salt | Mw acid | Mw salt | MS ES– |
|---|---|---|---|
| Esylate | 110.13 | 643.01 | 108.8 |
| | | | 531.1 |
| | | | 641.0 |
| Besylate | 158.18 | 691.06 | 156.8 |
| | | | 531.1 |
| | | | 689.2 |
| Cyclohexyl-sulphamate | 179.24 | 712.12 | 177.9 |
| | | | 531.2 |
| | | | 710.4 |
| Sulphate | 98.08 | 630.96 | 531.1 |
| Bromide | 80.91 | 613.79 | 531.2 |
| | | | 613.1 |
| p-Toluenesulphonate | 172.20 | 705.08 | 170.9 |
| | | | 531.1 |
| | | | 703.1 |
| 2-Naphtalenesulfonate | 208.24 | 741.12 | 206.9 |
| | | | 531.1 |
| | | | 739.3 |
| Hemisulfate | 98.07 | 1163.8 (1:2) | 531.1 |
| | | 630.85 (1:1) | 631.0 |
| Methanesulphonate | 96.11 | 628.99 | 531.1 |
| | | | 627.1 |
| Nitrate | 63.01 | 595.89 | 531.0 |
| | | | 594.0 |
| Hydrochloride | 36.46 | 569.34 | 531.0 |
| | | | 569.0 |

All salts formed in this Example were amorphous.

Example 18-B

Further amorphous salts of Compound B were made using analogous techniques to those described in Example 18-A above for the following acids:

1,2-Ethanedisulfonic (0.5 salt)

1S-Camphorsulfonic (+/−)-Camphorsulfonic p-Xylenesulfonic

2-Mesitylenesulfonic

Saccharin

Maleic

Phosphoric

D-glutamic

L-arginine

L-lysine

L-lysine*HCl

Example 18-C

Preparation of Amorphous Compound B, Hemi-1,5-naphthalenedisulfonic Acid Salt

Amorphous Compound B (110.9 mg) was dissolved in 2.5 mL 2-propanol and 0.5 equivalent of 1,5-naphthalene-disulfonic acid tetrahydrate was added (dissolved in 1 mL 2-propanol). The sample was stirred overnight. Only small particles (amorphous) or oil drops were observed by microscopy. The sample was evaporated to dryness.

Example 18-D

Preparation of Crystalline Compound B, Hemi-1,5-naphthalenedisulfonic Acid Salt

The crystallization experiment was carried out at ambient temperature, Amorphous Compound B (0.4 gram) was dissolved in ethanol (1.5 mL) and 0.5 eq of 1,5-naphthalene-disulfonic acid tetrahydrate (1.35 gram, 10% in ethanol) was added. Heptane (0.7 mL) was then added until the solution became slightly cloudy. After about 15 minutes the solution became turbid. After about 30 minutes thin slurry was obtained and additional heptane (1.3 mL) was added. The slurry was than left overnight for ripening. To dilute the thick slurry, a mixture of ethanol and heptane (1.5 mL and 1.0 mL respectively) was added. After about 1 hour the slurry was filtered and the crystals were washed with a mixture of ethanol and heptane (1.5:1) and finally with pure heptane. The crystals were dried at ambient temperature in 1 day. The dry crystals weighed 0.395 g.

Example 18-E

Preparation of Crystalline Compound B, Hemi-1,5-naphthalenedisulfonic Acid Salt

Amorphous Compound B (1.009 gr) was dissolved in 20 mL 2-propanol+20 mL ethyl acetate. 351.7 mg 1,5-naphtalene-disulfonic acid tetrahydrate, dissolved in 20 mL 2-propanol, was added drop by drop. Precipitation occurred in about 5 minutes. The slurry was stirred over night and then filtered.

Example 18-F

Preparation of Crystalline Compound B, Hemi-1,5-naphthalenedisulfonic Acid Salt 430.7 mg of the 1,5-naphtalene-disulfonic acid salt was dissolved in 30 mL 1-propanol. The solution was heated to boiling in order to dissolve the substance. The solution was left over night at ambient temperature for crystallization and then the crystals were filtered off.

Example 18-G

Preparation of Crystalline Compound B, Hemi-1,5-naphthalenedisulfonic Acid Salt

The mother liquid from Example 18-F was evaporated and the solid rest (61.2 mg) was dissolved in 6 mL acetonitrile/1-propanol, ratio 2:1. The solution was left overnight at ambient temperature to crystallize and then the crystals were filtered off.

Example 18-H

Preparation of Crystalline Compound B, Hemi-1,5-naphthalenedisulfonic Acid Salt

The sample from Example 18-C was dissolved in about 2 rap methanol, Ethanol (about 3 mL) was added as anti-solvent at ambient temperature and seeds were added. No crystallization occurred, so solvents were evaporated (about half of the amount) and a new portion of ethanol (about 2 nm) and seeds were added. Crystalline particles were formed when stirred at ambient temperature during night.

Example 18-I

Preparation of Crystalline Compound B, Hemi-1,5-naphthalenedisulfonic Acid Salt

Amorphous Compound B (104.1 mg) was dissolved in 2-propanol and 1 equivalent of 1,5-naphthalene-disulfonic acid tetrahydrate, dissolved in 2-propanol, was added In total, the 2-propanol amount was about 2.5 mL. The solution was stirred at 44° C. for about 80 minutes and a precipitate was formed. The particles were crystalline according to polarised light microscopy. The sample was filtered.

Example 18-J

Preparation of Crystalline Compound B, Hemi-1,5-naphthalenedisulfonic Acid Salt

Compound B, hemi-1,5-naphthalenedisulfonic acid salt (56.4 mg) was dissolved in 1.5 mL methanol. Methyl ethyl ketone (3 mL) was added. Seeds were added to the solution and crystallization started. The crystals were filtered off, washed with methyl ethyl ketone and air dried.

Example 18-K

Preparation of Crystalline Compound B, Hemi-1,5-naphthalenedisulfonic Acid Salt

Amorphous Compound B (161.0 mg) was dissolved in 3.5 mL 1-Butanol and the solution was heated to 40° C. In another beaker 57.4 mg of naphthalene-disulfonic acid tetrahydrate was dissolved in 3 mL 1-Butanol. A couple of drops of the acid solution were added to the solution of compound B. Then seeds were added to the solution and after 2 hours the rest of the acid solution was added (at 40° C.) slowly. Then the temperature was slowly decreased to room temperature and the experiment was left under stirring overnight. The slurry was filtered, washed with 1-Butanol and dried under vacuum at 44° C. for 2 hours. The yield was 83%.

Characterisation

Crystals of Compound B, hemi-1,5-naphthalenedisulfonic acid salt, obtained by way of Example 18-D above, was charaterised by NMR as follows:

21.3 mg of the salt was dissolved in deuterated methanol, 0.7 ml was investigated with NMR spectroscopy. A combination of 1D ($^1$H, $^{13}$C and selective NOE) and 2D (gCOSY, gHSQC and gHMBC) NMR experiments was used.

All data are in good agreement with the proposed structure, shown below. All carbons and the protons attached to carbons are assigned. Protons attached to heteroatoms are exchanged for deuterium from the solvent and are not detected. Most resonances in the 1D $^1$H and $^{13}$C NMR spectra are present as sets of two peaks. The reason for this is a slow rotation around the C9-N10 bond, which results in two atropisomers that simultaneously exist in the solution. The 1D NOE experiment is an evidence for this. When a resonance of one atropisomer is irradiated, the saturation is transferred to the corresponding peak of the other atropisomer. The resonances corresponding to the 1,5-naphtalenedisulfonate counter ion do not show atropisomerism.

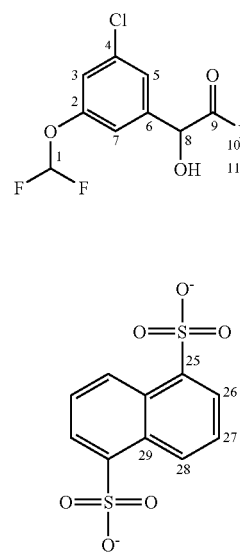

There are four fluorine atoms in the molecule. They give rise to split resonances for some protons and carbons. Both the proton and the carbon resonance corresponding to position 1 are split due to the spincoupling with the two fluorine nuclei in that position. The coupling constants are $^2J_{HF}$=73 Hz and $^1J_{CF}$=263 Hz. Further, the proton resonance corresponding to H19 is a distorted doublet with $^3J_{HF}$=6.9 Hz due to the spincoupling with the fluorine nuclei in position 18. Carbon resonances corresponding to C17, C18, C19 and C20 also exhibit couplings with these fluorine nuclei. The C17 and C20 resonances are triplets with $^2J_{CF}$=19 Hz and $^3J_{CF}$=11 Hz, respectively. The C18 resonance is a doublet of doublets with coupling constants $^1J_{CF}$=251 Hz and $^3J_{CF}$=8 Hz. The C19 resonance is a multiplet.

Comparing the magnitudes of integrals for resonances corresponding to the 1,5-naphtalenedisulfonate counter ion and the mother compound gives the stoichiometric relation of a single 1,5-naphtalenedisulfonate counter ion crystallized with two molecules of the mother compound.

$^1$H and $^{13}$C NMR chemical shift assignment and proton-proton correlations are shown in Table 11.

TABLE 11

| Atom No. | Type | $^{13}$C shift/ppm$^a$ | $^1$H shift/ppm$^b$ and multiplicity$^c$ | $J_{HH}$/Hz | Through-bond correlation to $^1$H$^d$ |
|---|---|---|---|---|---|
| 1 | CHF$_2$ | 117.5$^e$ | 6.91 (t) | 73 ($^2J_{HF}$) | nd |
| 1' | | 117.5$^e$ | 6.87 (t) | 73 ($^2J_{HF}$) | nd |
| 2 | C | 153.5 | na | na | na |
| 2' | | 153.3 | na | na | na |
| 3 | CH | 120.0 | 7.14 (t)$^n$ | nd | 5, 7 |
| 3' | | 119.6 | 7.11 (t)$^n$ | nd | 5', 7' |
| 4 | C | 136.1 | na | na | na |
| 4' | | 135.8 | na | na | na |
| 5 | CH | 125.0 | 7.31 (t)$^n$ | nd | 3, 7 |
| 5' | | 124.9 | 7.28 (t)$^n$ | nd | 3', 7' |
| 6 | C | 144.4 | na | na | na |
| 6' | | 145.3 | na | na | na |
| 7 | CH | 117.2 | 7.16 (t)$^n$ | nd | 3, 5 |
| 7' | | 117.1 | 7.12 (t)$^n$ | nd | 3', 5' |
| 8 | CH | 72.9 | 5.15 (s) | na | nd |
| 8' | | 73.6 | 5.07 (s) | na | nd |
| 9 | CO | 173.0 | na | na | na |
| 9' | | 173.5 | na | na | na |
| 11 | CH$_2$ | 51.5 | a: 4.29 (m) b: 4.13 (m) | nd | 12, 13 |
| 11' | | 48.6 | a: 4.01 (m) b: 3.93 (m) | nd | 12', 13' |
| 12 | CH$_2$ | 21.7 | a: 2.46 (m) b: 2.17 (m) | nd | 11, 13 |
| 12' | | 22.8 | a: 2.61 (m) b: 2.03 (m) | nd | 11', 13' |
| 13 | CH | 62.8 | 4.70 (dd) | 6.0 and 9.4 | 12 |
| 13' | | 65.8 | 5.14 (dd) | 5.6 and 9.1 | 12' |
| 14 | CO | 172.4 | na | na | na |
| 14' | | 173.2 | na | na | na |
| 16 | CH$_2$ | 32.3 | 4.51 (m) | nd | nd |
| 16' | | 32.5 | 4.51 (m) | nd | nd |
| 17 | C | 121.0$^f$ | na | na | na |
| 18 | CF | 162.8$^g$ | na | na | na |
| 19 | CH | 112.7$^i$ | 7.35 (d) | 6.9 ($^3J_{HF}$) | nd |
| 20 | C | 127.9$^k$ | na | na | na |
| 21 | C | 160.0 | na | na | na |
| 21' | | 159.9 | na | na | na |
| 24 | CH$_3$ | 64.8 | 3.93 (s) | na | nd |
| 24' | | 64.8 | 3.92 (s) | na | nd |
| 25 | C | 142.4 | na | na | na |
| 26 | CH | 126.8 | 8.16 (d) | 7.2 | 27, 28 |
| 27 | CH | 125.9 | 7.54 (dd) | 8.6 and 7.2 | 26, 28 |
| 28 | CH | 131.0 | 8.97 (d) | 8.6 | 26, 27 |
| 29 | C | 131.1 | na | na | na |

Figure 5:
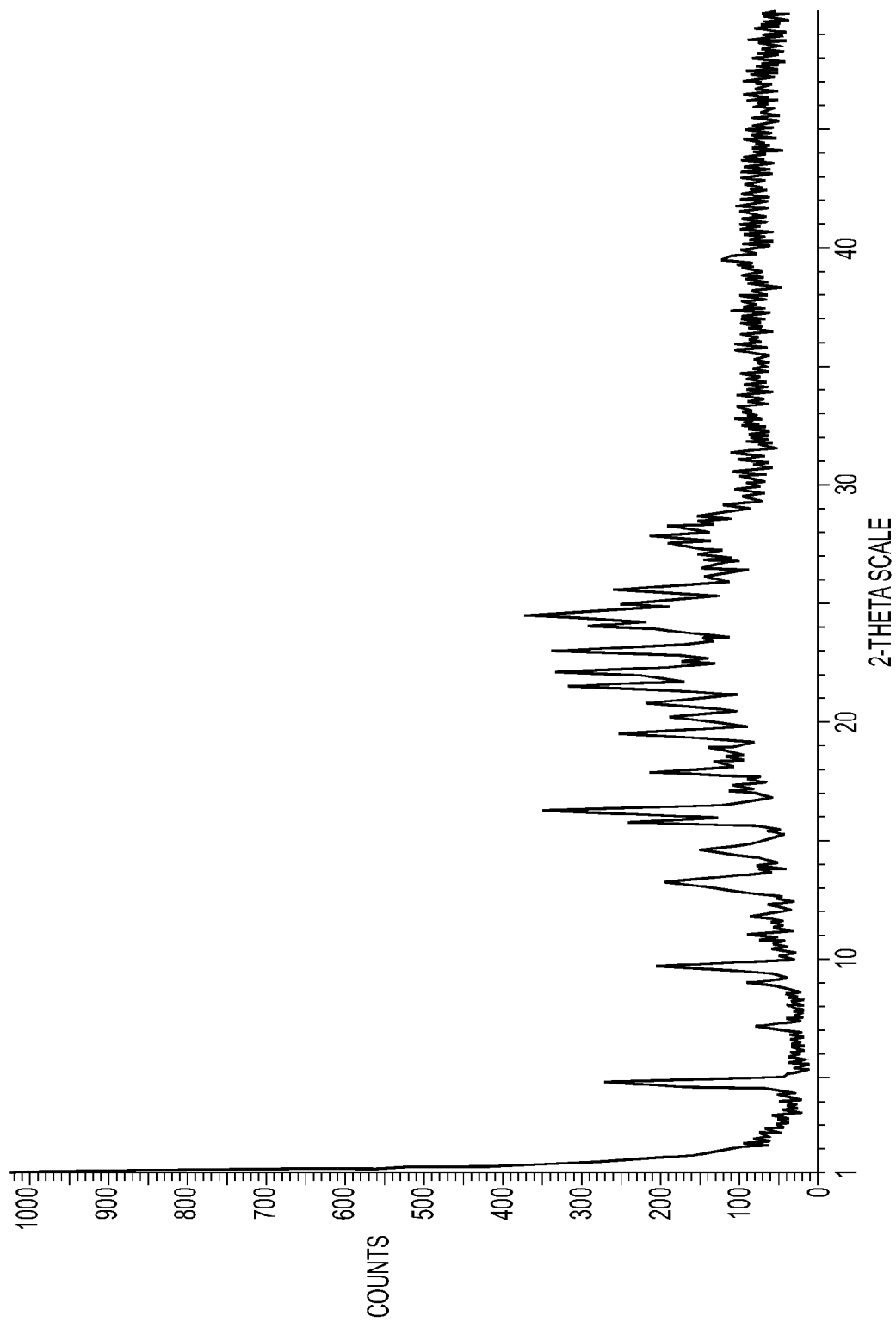
FIG. 5 shows an X-ray powder diffractogram for crystalline Compound B, hemi-1,5-naphthalenedisulfonic acid salt.

$^a$Relative to the solvent resonance at 49.0 ppm.
$^b$Relative to the solvent resonance at 3.30 ppm.
$^c$s = singlet, d = doublet, dd = doublet of doublets, t = triplet, m = multiplet.
$^d$Obtained in the gCOSY experiment.
$^e$The resonance is a triplet due to coupling with the two fluorine nuclei F1. $^1J_{CF}$ = 263 Hz.
$^f$The resonance is a triplet due to coupling to the two fluorine nuclei F18. $^2J_{CF}$ = 19 Hz.
$^g$The resonance is a doublet of doublets due to coupling to the two fluorine nuclei F18. $^1J_{CF}$ = 251 Hz and $^3J_{CF}$ = 8 Hz.
$^i$The resonance is a multiplet due to coupling to the two fluorine nuclei F18.
$^k$The resonance is a triplet due to coupling to the two fluorine nuclei F18. $^3J_{CF}$ = 11 Hz.
$^m$The $^4J_{HH}$ coupling with the meta-protons is not fully resolved.
na = not applicable,
nd = not determined Crystals of Compound B, hemi-1,5-naphthalenedisulfonic acid sat (obtained by way of Example 18-I above, were analyzed by XRPD and the results are tabulated below (Table 12) and are shown in FIG. 5.

TABLE 12

| d value (Å) | Intensity (%) | Intensity |
|---|---|---|
| 18.3 | 99 | vs |
| 12.5 | 22 | s |
| 9.9 | 22 | s |
| 9.1 | 67 | vs |
| 8.0 | 18 | m |
| 7.5 | 17 | m |
| 6.8 | 37 | s |
| 6.7 | 59 | s |
| 6.1 | 39 | s |
| 6.0 | 21 | s |
| 5.6 | 66 | vs |
| 5.5 | 98 | vs |
| 4.94 | 48 | s |
| 4.56 | 59 | s |
| 4.39 | 35 | s |
| 4.27 | 33 | s |
| 4.13 | 81 | vs |
| 4.02 | 87 | vs |
| 3.86 | 88 | vs |
| 3.69 | 69 | vs |
| 3.63 | 100 | vs |
| 3.57 | 49 | s |
| 3.48 | 53 | s |
| 3.23 | 35 | s |
| 3.19 | 43 | s |
| 3.16 | 38 | s |

DSC showed an endotherm with an extrapolated melting onset temperature of ca 183° C. and TGA showed a 0.3% weight loss between 25-110° C.

Example 19

Ph(3-Cl)(5-OCHF$_2$)—R)CH(OH)C(CO)—(S)Aze-Pab(OMe) Benzensulfonic Acid Salt

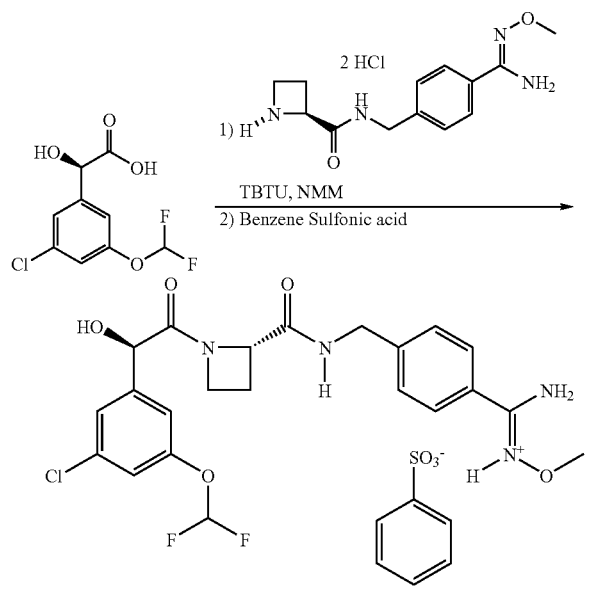

N-methylmorpholine: NMM 0-(1-H-benzotriazole-1-yl)-1,1,3,3-tetramethyluronium tetrafluoroborate: TBTU To a stirred solution of Ph(3-Cl)(5-OCHF$_2$)—(R)CH(OH)C(O)OH (12.6 g, 50 mmol) in ethyl acetate (126 ml) at 0° C. is added N-methylmorpholine (16.5 ml, 150 mmol), HAze-Pab(OMe).2HCl (16.8 g, 50 mmol; see Compound C (vi) description herein) and TBTU (16.7, 50 mmol). The reaction is allowed to warm to room temperature and is stirred overnight. The reaction mixture is washed with water, 15% w/v potassium carbonate solution, water, brine and water, dried and concentrated.

To the partially concentrated solution ethyl acetate (115 ml) is added a solution of benzene sulfonic acid (7.1 g, 45 mmol) in 2-propanol (38.4 ml) at 40° C. The solution was seeded and stirred for 2 hours at 40° C. followed by stirring overnight at room temperature. When precipitation of the besylate salt is complete the product is filtered, washed and dried under vacuum at 40° C., to afford the sub title compound (22.6 g, 69%).

Example 20

Ph(3-Cl(5-OCHF$_2$)—(R)CH(OH)C(O)—(S)Aze-Pab (2.6-diF OMe

The coupling reaction of Example 19 may be repeated using HAze-Pab(2,6-diF)(OMe), and the final product precipitated, for example, as the hemi-1,5-naphthalenedisulfonic acid salt.

To a stirred solution of Ph(3-Cl)(5-OCBF$_2$)—(R)CH(OH)C(O)OH (10.6 g, 42 mmol) in ethyl acetate (66 ml) at 0° C. is added N-methylmorpholine (6.2 g, 61.2 mmol), HAze-Pab (2,6-diF) (OMe) (readily prepared from Cpd B prep. (xi), 12.0 g, 38.2 mmol) and TBTU (15.3 g, 48 mmol). The reaction is allowed to warm to room temperature and is stirred overnight. The reaction mixture is washed with water, 15% w/v potassium carbonate solution (×2), water, brine and water, dried and partially concentrated. The solution is dried with anhydrous sodium sulfate (24 g), the drying agent filtered off and the filtrate concentrated down to a foam (12.2 g, 60%)

ABBREVIATIONS

Ac=acetyl
APCI=atmospheric pressure chemical ionisation (in relation to MS)
API=atmospheric pressure ionisation (in relation to MS)
aq.=aqueous
Aze(& (S)-Aze)=(S)-azetidine-2-carboxylate (unless otherwise specified)
Boc=tert-butyloxycarbonyl
br=broad (in relation to NMR)
CI=chemical ionisation (in relation to MS)
d=day(s)
d=doublet (in relation to NMR)
DCC=dicyclohexyl carbodiimide
dd=doublet of doublets (in relation to NMR)
DIBAL-H=di-isobutylaluminum hydride
DIPEA=diisopropylethylamine
DMAP=4-(N,N-dimethyl amino) pyridine
DMF=N,N-dimethylformamide
DMSO=dimethylsulfoxide
DSC=differential scanning calorimetry
DVT=deep vein thrombosis
EDC=1-(3-dimethylaminopropyl)-3-ethylcarbodiimide hydrochloride eq. equivalents
ES=electrospray
ESI=electrospray interface
Et=ethyl
ether=diethyl ether EtOAc=ethyl acetate
EtOH=ethanol
Bt₂O=diethyl ether
FT-IR=Fourier-transform infra-red spectroscopy
gCOSY=gradient-selective correlated spectroscopy
gHMC=gradient-selective heteronuclear multiple bond correlation spectroscopy
gHSQC=gradient-selective heteronuclear single quantum coherence
HATU=O-(azabenzotriazol-1-yl)-N,N,N',N'-tetramethyluronium hexafluorophosphate
HBTU=[N,N,N',N'-tetramethyl-O-(benzotriazol-1-yl)uronium hexafluorophosphate]
HCl=hydrochloric acid, hydrogen chloride gas or hydrochloride salt (depending on context)
Hex=hexanes
HOAc=acetic acid
HPLC=high performance liquid chromatography
LC=liquid chromatography
m=multiplet (in relation to NMR)
Me=methyl
MeOH=methanol
min.=minute(s)
MS=mass spectroscopy
MTBE=methyl tert-butyl ether
NOE=nuclear Overhauser enhancement
NMR=nuclear magnetic resonance
OAc=acetate
Pab=para-amidinobenzylamino
H-Pab=para-amidinobenzylamine
Pd/C=palladium on carbon
Ph=phenyl
PyBOP=(benzotriazol-1-yloxy)tripyrrolidinophosphonium hexafluorophosphate
q=quartet (in relation to NMR)
QF=tetrabutylammonium fluoride
rt/RT=room temperature
s=singlet (in relation to NMR)
t=triplet (in relation to NMR)
TUTU=[N,N,N',N'-tetramethyl-O-(benzotriazol-1-yl)uronium tetrafluoroborate]
TEA=triethylamine
Teoc=2-(trimethylsilyl)ethoxycarbonyl
TEMPO=2,2,6,6-tetramethyl-1-piperidinyloxy free radical
TFA=trifluoroacetic acid
TGA=thermogravimetric analysis
THF=tetrahydrofuran
TLC=thin layer chromatography
UV=ultraviolet
XRPD=X-ray powder diffraction Prefixes n-, s-, i-, t- and tert- have their usual meanings: normal, secondary, iso, and tertiary.

Particular aspects of the invention are provided as follows:—

When aspects refer to other aspects, this reference also includes sub-aspects. For example, reference to aspect 14 includes reference to aspects 14 and 14A.

1. A pharmaceutically-acceptable acid addition salt of a compound of formula I, wherein $R^1$ represents $C_{1-2}$ alkyl substituted by one or more fluoro substituents;

$R^2$ represents $C_{1-2}$ alkyl; and n represents 0, 1 or 2.

2. A compound as described in aspect 1, wherein the acid is an organic acid.

3. A compound as described in aspect 2, wherein the acid is a sulfonic acid.

4. A compound as described in aspect 3, wherein the acid is 1,2-ethanedisulfonic acid, a camphorsulfonic acid, ethanesulfonic acid, a propanesulfonic acid, a butanesulfonic acid, a pentanesulfonic acid, a toluenesulfonic acid, methanesulfonic acid, p-xylenesulfonic acid, 2-mesitylenesulfonic acid, a naphthalenesulfonic acid, benzenesulfonic acid, a hydroxybenzenesulfonic acid, 2-hydroxyethanesulfonic acid or 3-hydroxyethanesulfonic acid.

5. A compound as described in aspect 3, wherein the acid is a $C_{1-6}$ alkanesulfonic acid or an optionally substituted arylsulfonic acid or an optionally substituted aryldisulfonic acid, 6. A compound as described in aspect 4 or aspect 5, wherein the acid is ethanesulfonic acid, n-propanesulfonic acid or benzenesulfonic acid.

6A. A compound as described in aspect 4 or aspect 5, wherein the acid is ethanesulfonic acid, n-propanesulfonic acid, benzenesulfonic acid, 1,5-naphthalenedisulfonic acid, or n-butanesulfonic acid.

7. A compound as described in any one of aspects 1 to 6, wherein $R^1$ represents —OCHF₂ or —OCH₂CH₂F.

8. A compound as described in any one of aspects 1 to 7, wherein $R^2$ represents methyl.

9. A compound as described in any one of aspects 1 to 8, wherein n represents 0 or 2.

10. A compound as described in aspect 9, wherein, when n represents 2, the two fluoro atoms are located at the two ortho-positions relative to the point of attachment of the benzene ring to the —NH—CH₂— group.

11. A compound as described in any one of aspects 1 to 10, wherein the compound of formula I is Ph(3-Cl)(5-OCHF₂)—(R)CH(OH)C(O)—(S)Aze-Pab(OMe).

12. A compound as described in any one of aspects 1 to 10, wherein the compound of formula I is Ph(3-Cl)(5-OCHF₂)—(R)CH(OH)C(O)—(S)Aze-Pab(2,6-diF)(OMe).

13. A compound as described in any one of aspects 1 to 10, wherein the compound of formula I is Ph(3-Cl)(5-OCH$_2$CH$_2$F)—(R)CH(OH)C(O)— (S)Aze-Pab(OMe).

14. A compound as described in any one of aspects 1 to 13 in substantially crystalline form.

14A. A compound as described in any one of aspects 1 to 13 in partially crystalline form.

15. A compound as described in any one of aspects 1 to 9, 11 or 14, which is Ph(3-Cl)(5-OCHF$_2$)—(R)CH(OH)C(O)—(S)Aze-Pab(OMe), ethanesulfonic acid salt.

16. A compound as described in aspect 15, characterised by a differential scanning calorimetry curve, at a heating rate of 10° C./min in a closed pan with a pinhole under flowing nitrogen, exhibiting an endotherm with an extrapolated onset temperature of about 131° C.; and/or an X-ray powder diffraction pattern characterised by peaks with d-values at 16.5, 12.2, 9.0, 7.6, 6.2, 6.0, 5.9, 5.5, 5.4, 5.1, 4.66, 4.60, 4.31, 4.25, 4.19, 4.13, 4.00, 3.87, 3.83, 3.76, 3.72, 3.57, 3.51, 3.47, 3.31, 3.26, 3.21, 3.03, 2.74, 2.56, 2.50, 2.46 and 2.21 Å, and/or essentially as defined in Table 3 and/or in FIG. 1.

16A. A compound as described in aspect 16, characterised by an X-ray powder diffraction pattern characterised by peaks with strong and very strong intensity as defined in Table 3.

17. A compound as described in any one of aspects 1 to 9, 11 or 14, which is Ph(3-Cl)(5-OCHF$_2$)—(R)CH(OH)C(O)—(S)Aze-Pab(OMe), benzene-sulfonic acid salt.

18. A compound as described in aspect 17, characterised by a differential scanning calorimetry curve, at a heating rate of 10° C./min in a closed pan with a pinhole under flowing nitrogen, exhibiting an endotherm with an extrapolated onset temperature of about 152° C.; and/or an X-ray powder diffraction pattern characterised by peaks with devalues at 14.2, 12.6, 10.2, 7.5, 6.4, 6.3, 6.1, 5.9, 5.7, 5.4, 5.3, 5.1, 4.83, 4.73, 4.54, 4.50, 4.35, 4.30, 4.24, 4.17, 4.09, 4.08, 3.96, 3.91, 3.77, 3.62, 3.52, 3.31, 3.19, 3.15, 3.09, 3.00, 2.79, 2.76, 2.72, 2.59, 2.56, 2.54, 2.49 and 2.38 Å, and/or essentially as defined in Table 5 and/or in FIG. 2.

18A. A compound as described in aspect 18, characterised by an X-ray powder diffraction pattern characterised by peaks with strong and very strong intensity as defined in Table 5.

19. A compound as described in any one of aspects 1 to 9, 11 or 14, which is Ph(3-Cl)(5-OCHF$_2$)—(R)CH(OH)C(O)—(S)Aze-Pab(OMe), n-propane-sulfonic acid salt.

20. A compound as described in aspect 19, characterised by a differential scanning calorimetry curve, at a heating rate of 10° C./min in a closed pan with a pinhole under flowing nitrogen, exhibiting an endotherm with an extrapolated onset temperature of about 135° C.; and/or an X-ray powder diffraction pattern characterised by peaks with devalues at 12.4, 10.0, 7.5, 6.2, 5.8, 5.7, 5.4, 5.3, 4.78, 4.68, 4.51, 4.49, 4.40, 4.32, 4.29, 4.25, 4.19, 4.14, 4.07, 4.04, 3.94, 3.88, 3.73, 3.48, 3.28, 2.97, 2.54, 2.51 and 2.46 Å, and/or essentially as defined in Table 7 and/or in FIG. 3.

20A. A compound as described in aspect 207 characterised by an X-ray powder diffraction pattern characterised by peaks with strong and very strong intensity as defined in Table 7.

20.B A compound as described in any one of aspects 1 to 10, 12, 14 or 14A, wherein the compound of formula I is Ph(3-Cl)(5-OCHF$_2$)—(R)CH(OH)C(O)—(S)Aze-Pab(2,6-diF)(OMe), hemi-1,5-naphthalenedisulfonic acid salt.

20C. A compound as described in aspect 201, characterised by an X-ray powder diffraction pattern characterised by peaks with strong and very strong intensity as defined in Table 12.

21. A process for the preparation of a compound as described in any one of aspects 1 to 20, which process comprises addition of an acid to a compound of is formula I as defined in aspect 1.

22. A process for the preparation of a compound as described in aspect 14, or any one of aspects 15 to 20 (as dependent on aspect 14), which process comprises crystallising a compound as described in any one of aspects 1 to 13.

23. A process for the preparation of a compound as described in aspect 14, or any one of aspects 15 to 20 (as dependent on aspect 14), which process comprises a process as described in aspect 21 followed by a process as described in aspect 22.

24. A process as described in aspect 22 or aspect 23, which comprises crystallising the compound from a solvent, 25. A process as described in aspect 24, wherein the solvent is selected from the group: lower alkyl acetates, lower alkyl alcohols, lower dialkyl ketones, aliphatic hydrocarbons and aromatic hydrocarbons.

26. A process as described in aspect 24, which comprises dissolving a compound as defined in aspect 1 in amorphous form in a solvent selected from the group lower alkyl alcohols, lower alkyl acetates, lower dialkyl ketones, and mixtures thereof, and subsequent crystallisation.

27. A process as described in aspect 26 which comprises either:
(a) dissolving the compound in a lower alkyl alcohol, and then addition of a lower alkyl acetate or a lower dialkyl ketone; or
(b) dissolving the compound in a mixture of a lower alkyl alcohol and a lower alkyl acetate, or a mixture of a lower alkyl alcohol and a lower dialkyl ketone.

28. A process as described in aspect 27 wherein the solvents are selected from the group: methyl iso-butyl ketone, iso-propanol, ethyl acetate, iso-propyl acetate and mixtures thereof.

29. A process as described in aspect 24, which comprises a process as described in aspect 21, followed by direct crystallisation of the compound so formed from a solvent system that comprises a lower alkyl acetate, a lower dialkyl ketone or a hydrocarbon, 30. A process as described in aspect 29 wherein the solvent system is selected from the group: iso-propanol, iso-propyl acetate, n-butyl acetate, toluene, methyl iso-butyl ketone, ethyl acetate and mixtures thereof.

31. A process as described in aspect 24, which comprises pre-forming compound of formula I in a lower alkyl alcohol, followed by addition of a lower alkyl acetate, a lower dialkyl ketone or a hydrocarbon, 31A. A process as described in any of aspects 25 to 31, wherein the term lower alkyl denotes linear or branched (1-4C)alkyl.

32. A process as described in aspect 31 wherein the solvents are selected from the group: methanol, ethanol, iso-propanol, methyl iso-butyl ketone, n-butyl acetate, toluene, iso-octane, n-heptane, ethyl acetate and iso-propyl acetate.

33. A process for the preparation of a crystalline compound as defined in aspect 15 or aspect 16, which comprises slurrying pre-formed salt in either methyl iso-butyl ketone or a mixture of iso-propanol and ethyl acetate.

34. A process for the preparation of a crystalline compound as defined in aspect 15 or aspect 16, which comprises adding ethanesulfonic acid (optionally in the form of a solution in methyl iso-butyl ketone) to a solution of Ph(3-Cl)(5-OCHF$_2$)—(R)CH(OH)C(O)—(S)Aze-Pab(OMe) in methyl iso-butyl ketone.

35. A process for the preparation of a crystalline compound as defined in aspect 15 or aspect 16, which comprises adding ethanesulfonic acid to a solution of Ph(3-Cl)(5-OCHF$_2$)—(R)CH(OH)C(O)—(S)Aze-Pab(OMe) in iso-propanol, and then adding ethyl acetate as antisolvent.

36. A process for the preparation of a crystalline compound as defined in aspect 17 or aspect 18, which comprises slurrying pre-formed salt in ethyl acetate, methyl iso-butyl ketone or iso-propyl acetate.

37. A process for the preparation of a crystalline compound as defined in aspect 17 or aspect 18, which comprises adding benzenesulfonic acid to a solution of Ph(3-Cl)(5-OCHF$_2$)—(R)CH(OH)C(O)—(S)Aze-Pab(OMe) in ethyl acetate and then adding iso-propanol to facilitate crystallisation.

38. A process for the preparation of a crystalline compound as defined in aspect 17 or aspect 18, which comprises adding benzenesulfonic acid to a solution of Ph(3-Cl)(5-OCF$_2$)—(R)CH(OH)C(O)—(S)Aze-Pab(OMe) in iso-propanol and then adding ethyl acetate as antisolvent.

39. A process for the preparation of a crystalline compound as defined in aspect 19 or aspect 20, which comprises slurrying pre-formed salt in a mixture of iso-propanol and iso-propyl acetate, or in a mixture of iso-propanol and ethyl acetate.

40. A process for the preparation of a crystalline compound as defined in aspect 19 or aspect 20, which comprises adding n-propanesulfonic acid to a solution of Ph(3-Cl)(5-OCHF$_2$)—(R)CH(OH)C(O)—(S)Aze-Pab(OMe) in iso-propanol and then adding ethyl acetate, or iso-propyl acetate, as antisolvent.

41. A compound obtainable by a process according to any one of aspects 21 to 40.

42. A compound as described in any one of aspects 1 to 20 or 41 for use as a medicament.

43. A pharmaceutical formulation including a compound as defined in any one of aspects 1 to 20 or 41 in admixture with a pharmaceutically acceptable adjuvant, diluent or carrier.

44. A compound as defined in any one of aspects 1 to 20 or 41, or a pharmaceutically acceptable derivative thereof, for use as a pharmaceutical.

45. A compound as defined in any one of aspects 1 to 20 or 41, or a pharmaceutically acceptable derivative thereof, for use in the treatment of a condition where inhibition of thrombin is required.

46. A compound as defined in any one of aspects 1 to 20 or 41, or a pharmaceutically acceptable derivative thereof, for use in the treatment of a condition where anticoagulant therapy is indicated.

47. A compound as defined in any one of aspects 1 to 20 or 41, or a pharmaceutically acceptable derivative thereof, for use in the treatment of thrombosis.

48. A compound as defined in any one of aspects 1 to 20 or 41, or a to pharmaceutically acceptable derivative thereof, for use as an anticoagulant.

49. The use of a compound as defined in any one of aspects 1 to 20 or 41, or a pharmaceutically acceptable derivative thereof, as an active ingredient for the manufacture of a medicament for the treatment of a condition where inhibition of thrombin is required.

50. The use of a compound as defined in any one of aspects 1 to 20 or 41, or a pharmaceutically acceptable derivative thereof, as an active ingredient for the manufacture of a medicament for the treatment of a condition where anticoagulant therapy is indicated.

51. The use as described in aspect 49 or aspect 50, wherein the condition is thrombosis.

52. The use as described in aspect 49 or aspect 50, wherein the condition is hypercoagulability in blood and/or tissues.

53. The use of a compound as defined in any one of aspects 1 to 20 or 41, or a pharmaceutically acceptable derivative thereof as an active ingredient for the manufacture of an anticoagulant.

54. A method of treatment of a condition where inhibition of thrombin is required which method comprises administration of a therapeutically effective amount of a compound as defined in any one of aspects 1 to 20 or 41, or a pharmaceutically acceptable derivative thereof, to a person suffering from, or susceptible to, such a condition.

55. A method of treatment of a condition where anticoagulant therapy is indicated which method comprises administration of a therapeutically effective amount of a compound as defined in any one of aspects 1 to 20 or 41, or a pharmaceutically acceptable derivative thereof, to a person suffering from, or susceptible to, such a condition.

56. A method as described in aspect 54 or aspect 55, wherein the condition is thrombosis.

57. A method as described in aspect 54 or aspect 55, wherein the condition is hypercoaguability in blood and/or tissues.

The invention claimed is:

1. A method of treating a condition where inhibition of thrombin is required, comprising administering to a mammal suffering from such a condition a therapeutically effective amount of a sulfonic acid addition salt in crystalline form of a compound of formula I

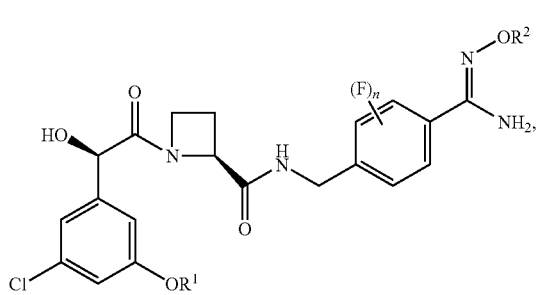

wherein:
R$^1$ is C$_{1-2}$ alkyl substituted with one or more fluoro substituents;
R$^2$ is C$_{1-2}$ alkyl; and
n is 0, 1, or 2.

2. A method of inhibiting thrombin in a mammal susceptible to a condition where inhibition of thrombin is required, comprising administering to the mammal a prophylactically effective amount of a sulfonic acid addition salt in crystalline form of a compound of formula I

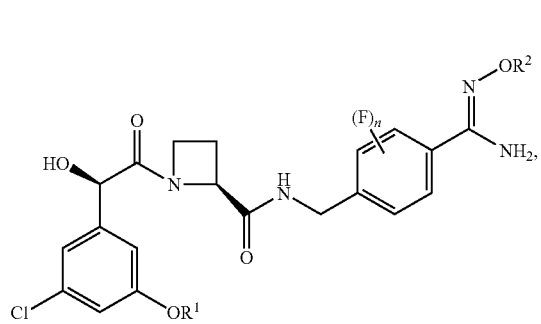

wherein:
R$^1$ is C$_{1-2}$ alkyl substituted with one or more fluoro substituents;
R$^2$ is C$_{1-2}$ alkyl; and
n is 0, 1, or 2.

3. The method as claimed in claim 1 or claim 2, wherein the condition is thrombosis.

4. The method as claimed in claim 1 or claim 2, wherein the condition is hypercoagulability in blood and/or tissues.

5. The method as claimed in claim 1 or claim 2, wherein the condition is venous thrombosis.

6. The method as claimed in claim 5, wherein the venous thrombosis is deep vein thrombosis.

7. The method as claimed in claim 1 or claim 2, wherein the condition is pulmonary embolism or arterial thrombosis.

8. The method as claimed in claim 1 or claim 2, wherein the condition is thrombosis-based stroke.

9. The method as claimed in claim 1 or claim 2, wherein the condition is atrial fibrillation.

10. The method as claimed in claim 1 or claim 2, wherein the condition is non-valvular atrial fibrillation.

11. The method as claimed in claim 1 or claim 2, wherein the compound is combined and/or co-administered with at least one of
antiplatelet agents, wherein the antiplatelet agents are selected from the group consisting of acetylsalicylic acid, ticlopidine and clopidogrel;
thromboxane receptor and/or synthetase inhibitors;
fibrinogen receptor antagonists;
prostacyclin mimetics;
phosphodiesterase inhibitors;
ADP-receptor (P$_2$T) antagonists; and
inhibitors of carboxypeptidase U (CPU).

12. The method as claimed in claim 1 or claim 2, wherein the compound is combined and/or co-administered with an antiplatelet agent, wherein the antiplatelet agent is acetylsalicylic acid.

13. A method of treating a condition where anticoagulant therapy is indicated, comprising administering to a mammal suffering from such a condition a therapeutically effective amount of a sulfonic acid addition salt in crystalline form of a compound of formula I

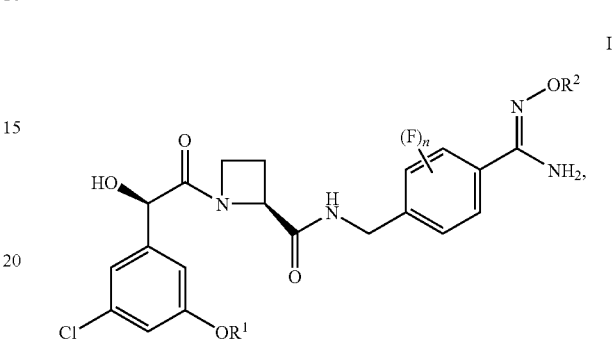

wherein:
R$^1$ is C$_{1-2}$ alkyl substituted with one or more fluoro substituents;
R$^2$ is C$_{1-2}$ alkyl; and
n is 0, 1, or 2.

14. The method as claimed in any one of claims 1, 2 and 13, wherein the mammal is a human.

15. The method as claimed in claim 1 or claim 2, wherein the sulfonic acid is methanesulfonic acid, n-propanesulfonic acid, benzenesulfonic acid, 1,5-naphthalenedisulfonic acid, or n-butanesulfonic acid.

16. The method as claimed in claim 1 or claim 2, wherein R$^1$ is —CHF$_2$ or —CH$_2$CH$_2$F.

17. The method as claimed in claim 1 or claim 2, wherein R$^2$ is methyl.

18. The method as claimed in claim 1 or claim 2, wherein n is 0 or 2.

19. The method as claimed in any one of claims 1, 2 and 13, wherein the compound of formula I is Ph(3-Cl)(5-OCHF$_2$)—(R)CH(OH)C(O)—(S)Aze-Pab(OMe) or Ph(3-Cl)(5-OCHF$_2$)—(R)CH(OH)C(O)—(S)Aze-Pab(2,6-diF)(OMe).

20. The method as claimed in any one of claims 1, 2 and 13, wherein the sulfonic acid addition salt is in substantially crystalline form.

21. The method as claimed in any one of claims 1, 2 and 13, wherein the sulfonic acid addition salt is in substantially crystalline form.

22. The method as claimed in any one of claims 1, 2 and 13, wherein the sulfonic acid addition salt is Ph(3-Cl)(5-OCHF$_2$)—(R)CH(OH)C(O)—(S)Aze-Pab(OMe) benzenesulfonic acid salt.

* * * * *